(12) United States Patent
Bennett et al.

(10) Patent No.: US 8,308,771 B2
(45) Date of Patent: Nov. 13, 2012

(54) METHODS AND APPARATUS FOR LOCKING A BAND

(75) Inventors: Ian Bennett, San Francisco, CA (US); Louis Fielding, San Carlos, CA (US); Hugues Malandain, Mountain View, CA (US); Todd Alamin, Woodside, CA (US)

(73) Assignee: Simpirica Spine, Inc., San Carlos, CA (US)

( * ) Notice: Subject to any disclaimer, the term of this patent is extended or adjusted under 35 U.S.C. 154(b) by 460 days.

(21) Appl. No.: 12/479,016

(22) Filed: Jun. 5, 2009

(65) Prior Publication Data

US 2010/0023060 A1    Jan. 28, 2010

Related U.S. Application Data

(60) Provisional application No. 61/059,538, filed on Jun. 6, 2008.

(51) Int. Cl.
*A61B 17/70* (2006.01)
(52) U.S. Cl. ............................................. 606/263
(58) Field of Classification Search ........... 606/246–279
See application file for complete search history.

(56) References Cited

U.S. PATENT DOCUMENTS

| | | | |
|---|---|---|---|
| 3,648,691 A | 3/1972 | Lumb et al. | |
| 3,754,733 A * | 8/1973 | Foster | 24/68 R |
| 4,246,660 A | 1/1981 | Wevers | |
| 4,643,178 A | 2/1987 | Nastari et al. | |
| 4,708,132 A | 11/1987 | Silvestrini | |
| 4,743,260 A | 5/1988 | Burton | |
| 4,772,286 A | 9/1988 | Goble et al. | |
| 4,776,851 A | 10/1988 | Bruchman et al. | |
| 4,794,916 A | 1/1989 | Porterfield et al. | |
| 4,870,957 A | 10/1989 | Goble et al. | |
| 4,955,910 A | 9/1990 | Bolesky | |

(Continued)

FOREIGN PATENT DOCUMENTS

EP    0 322 334 A1    6/1989

(Continued)

OTHER PUBLICATIONS

International Search Report and Written Opinion of PCT Application No. PCT/US2009/046501, mailed on Jul. 28, 2009, 12 pages total.

(Continued)

*Primary Examiner* — Alvin Stewart
*Assistant Examiner* — Summer Kostelnik
(74) *Attorney, Agent, or Firm* — Wilson, Sonsini, Goodrich & Rosati

(57) ABSTRACT

A surgical fastening mechanism for releasably locking an implantable tether includes a housing having a central channel. The housing has an entry aperture, an exit aperture and a side channel extending therebetween. A roller element has a sidewall with an aperture therethrough and the roller is slidably disposed at least partially in the central channel such that the entry and exit apertures are at least partially aligned with the roller aperture. This permits passage of the tether therethrough. Rotation of the roller element in a first direction winds the tether around the roller thereby creating a friction interface between the roller element, the housing and the tether. A locking mechanism is operably connected with either the housing or the roller element and is adapted to prevent rotation of the roller in the central channel and also adapted to prevent release of the tether from the roller.

101 Claims, 18 Drawing Sheets

U.S. PATENT DOCUMENTS

| | | |
|---|---|---|
| 4,966,600 A | 10/1990 | Songer et al. |
| 5,002,574 A | 3/1991 | May et al. |
| 5,011,484 A | 4/1991 | Breard |
| 5,011,494 A | 4/1991 | von Recum et al. |
| 5,092,866 A | 3/1992 | Breard et al. |
| 5,108,433 A | 4/1992 | May et al. |
| 5,116,340 A | 5/1992 | Songer et al. |
| 5,171,280 A | 12/1992 | Baumgartner |
| 5,180,393 A | 1/1993 | Commarmond |
| 5,282,863 A | 2/1994 | Burton |
| 5,354,917 A | 10/1994 | Sanderson et al. |
| 5,395,374 A | 3/1995 | Miller et al. |
| 5,415,658 A | 5/1995 | Killpela et al. |
| 5,415,661 A | 5/1995 | Holmes |
| 5,449,361 A | 9/1995 | Preissman |
| 5,456,722 A | 10/1995 | McLeod et al. |
| 5,458,601 A | 10/1995 | Young, Jr. et al. |
| 5,462,542 A | 10/1995 | Alesi, Jr. |
| 5,496,318 A | 3/1996 | Howland et al. |
| 5,540,698 A | 7/1996 | Preissman |
| 5,562,737 A | 10/1996 | Graf |
| 5,609,634 A | 3/1997 | Voydeville |
| 5,628,756 A | 5/1997 | Barker, Jr. et al. |
| 5,645,084 A | 7/1997 | McKay |
| 5,645,599 A | 7/1997 | Samani |
| 5,669,917 A | 9/1997 | Sauer et al. |
| 5,672,175 A | 9/1997 | Martin |
| 5,707,379 A | 1/1998 | Fleenor et al. |
| 5,725,582 A | 3/1998 | Bevan et al. |
| 5,902,305 A | 5/1999 | Beger et al. |
| 5,928,232 A | 7/1999 | Howland et al. |
| 5,933,452 A | 8/1999 | Eun |
| 5,935,133 A | 8/1999 | Wagner et al. |
| 5,964,769 A | 10/1999 | Wagner et al. |
| 5,989,256 A | 11/1999 | Kuslich et al. |
| 6,053,921 A | 4/2000 | Wagner et al. |
| 6,193,721 B1 | 2/2001 | Michelson |
| 6,224,630 B1 | 5/2001 | Bao et al. |
| 6,248,106 B1 | 6/2001 | Ferree |
| 6,283,996 B1 | 9/2001 | Chervitz et al. |
| 6,296,643 B1 | 10/2001 | Hopf et al. |
| 6,312,431 B1 | 11/2001 | Asfora |
| 6,322,279 B1 | 11/2001 | Yamamoto et al. |
| 6,364,883 B1 | 4/2002 | Santilli |
| 6,378,289 B1 | 4/2002 | Trudeau et al. |
| 6,391,030 B1 | 5/2002 | Wagner et al. |
| 6,395,018 B1 | 5/2002 | Castaneda |
| 6,436,099 B1 | 8/2002 | Drewry et al. |
| 6,451,019 B1 | 9/2002 | Zucherman et al. |
| 6,468,309 B1 | 10/2002 | Lieberman |
| 6,517,578 B2 | 2/2003 | Hein |
| 6,558,389 B2 | 5/2003 | Clark et al. |
| 6,582,433 B2 | 6/2003 | Yun |
| 6,605,091 B1 | 8/2003 | Iwanski |
| 6,616,669 B2 | 9/2003 | Ogilvie et al. |
| 6,626,944 B1 | 9/2003 | Taylor |
| 6,629,975 B1 | 10/2003 | Kilpela et al. |
| 6,652,527 B2 | 11/2003 | Zucherman et al. |
| 6,652,585 B2 | 11/2003 | Lange |
| 6,656,185 B2 | 12/2003 | Gleason et al. |
| 6,669,729 B2 | 12/2003 | Chin |
| 6,682,533 B1 | 1/2004 | Dinsdale et al. |
| 6,689,140 B2 | 2/2004 | Cohen |
| 6,689,168 B2 | 2/2004 | Lieberman |
| 6,695,852 B2 | 2/2004 | Gleason |
| 6,712,819 B2 | 3/2004 | Zucherman et al. |
| 6,716,245 B2 | 4/2004 | Pasquet et al. |
| 6,761,720 B1 | 7/2004 | Senegas |
| 6,828,357 B1 | 12/2004 | Martin et al. |
| 6,835,205 B2 | 12/2004 | Atkinson et al. |
| 6,899,716 B2 | 5/2005 | Cragg et al. |
| 7,029,475 B2 | 4/2006 | Panjabi |
| 7,163,558 B2 | 1/2007 | Senegas et al. |
| 7,201,751 B2 | 4/2007 | Zucherman et al. |
| 7,452,351 B2 | 11/2008 | Miller et al. |
| 7,458,981 B2 | 12/2008 | Fielding et al. |
| 7,520,887 B2 | 4/2009 | Maxy et al. |
| 7,524,324 B2 | 4/2009 | Winslow |
| 7,553,320 B2 | 6/2009 | Molz, IV et al. |
| 7,591,837 B2 | 9/2009 | Goldsmith |
| 2002/0095154 A1 | 7/2002 | Atkinson et al. |
| 2002/0147449 A1 | 10/2002 | Yun |
| 2002/0151978 A1 | 10/2002 | Zacouto et al. |
| 2003/0088251 A1 | 5/2003 | Braun et al. |
| 2004/0024458 A1 | 2/2004 | Senegas et al. |
| 2004/0106995 A1 | 6/2004 | Le Couedic et al. |
| 2004/0116927 A1 | 6/2004 | Graf |
| 2004/0117017 A1 | 6/2004 | Pasquet et al. |
| 2004/0127989 A1 | 7/2004 | Dooris et al. |
| 2004/0143268 A1 | 7/2004 | Falahee |
| 2004/0167520 A1 | 8/2004 | Zucherman et al. |
| 2004/0172132 A1 | 9/2004 | Ginn |
| 2004/0215341 A1 | 10/2004 | Sybert et al. |
| 2004/0243239 A1 | 12/2004 | Taylor |
| 2005/0033435 A1 | 2/2005 | Belliard et al. |
| 2005/0049708 A1 | 3/2005 | Atkinson et al. |
| 2005/0123581 A1 | 6/2005 | Ringeisen et al. |
| 2005/0131405 A1 | 6/2005 | Molz, IV et al. |
| 2005/0154390 A1 | 7/2005 | Biedermann et al. |
| 2005/0192581 A1 | 9/2005 | Molz et al. |
| 2005/0216017 A1 | 9/2005 | Fielding et al. |
| 2005/0267470 A1 | 12/2005 | McBride |
| 2005/0267518 A1 | 12/2005 | Wright et al. |
| 2006/0036324 A1 | 2/2006 | Sachs et al. |
| 2006/0041259 A1 | 2/2006 | Paul et al. |
| 2006/0064166 A1 | 3/2006 | Zucherman et al. |
| 2006/0069447 A1 | 3/2006 | Disilvestro et al. |
| 2006/0084976 A1 | 4/2006 | Borgstrom et al. |
| 2006/0106381 A1 | 5/2006 | Ferree et al. |
| 2006/0106397 A1 | 5/2006 | Lins |
| 2006/0136060 A1 | 6/2006 | Taylor |
| 2006/0142760 A1 | 6/2006 | McDonnell |
| 2006/0149230 A1 | 7/2006 | Kwak et al. |
| 2006/0195102 A1 | 8/2006 | Malandain |
| 2006/0217726 A1 | 9/2006 | Maxy et al. |
| 2006/0240533 A1 | 10/2006 | Sengupta et al. |
| 2006/0241610 A1 | 10/2006 | Lim et al. |
| 2006/0247635 A1* | 11/2006 | Gordon et al. .................. 606/61 |
| 2006/0271055 A1 | 11/2006 | Thramann |
| 2007/0010822 A1 | 1/2007 | Zalenski et al. |
| 2007/0073293 A1 | 3/2007 | Martz et al. |
| 2007/0083200 A1 | 4/2007 | Gittings et al. |
| 2007/0213829 A1 | 9/2007 | Le Couedic et al. |
| 2007/0233096 A1 | 10/2007 | Garcia-Bengochea |
| 2007/0270828 A1 | 11/2007 | Bruneau et al. |
| 2007/0299445 A1 | 12/2007 | Shadduck et al. |
| 2008/0009866 A1 | 1/2008 | Alamin et al. |
| 2008/0021466 A1 | 1/2008 | Shadduck et al. |
| 2008/0027435 A1 | 1/2008 | Zucherman et al. |
| 2008/0033552 A1 | 2/2008 | Lee et al. |
| 2008/0045949 A1 | 2/2008 | Hunt et al. |
| 2008/0051784 A1 | 2/2008 | Gollogly |
| 2008/0097431 A1 | 4/2008 | Vessa |
| 2008/0108993 A1 | 5/2008 | Bennett et al. |
| 2008/0114357 A1 | 5/2008 | Allard et al. |
| 2008/0125780 A1 | 5/2008 | Ferree |
| 2008/0177264 A1 | 7/2008 | Alamin et al. |
| 2008/0177298 A1 | 7/2008 | Zucherman et al. |
| 2008/0183209 A1 | 7/2008 | Robinson et al. |
| 2008/0262549 A1 | 10/2008 | Bennett et al. |
| 2008/0281423 A1 | 11/2008 | Sheffer et al. |
| 2008/0312693 A1 | 12/2008 | Trautwein et al. |
| 2008/0319487 A1 | 12/2008 | Fielding et al. |
| 2009/0030457 A1 | 1/2009 | Janowski et al. |
| 2009/0082820 A1 | 3/2009 | Fielding et al. |
| 2009/0118766 A1 | 5/2009 | Park et al. |
| 2009/0198282 A1 | 8/2009 | Fielding et al. |
| 2009/0264929 A1 | 10/2009 | Alamin et al. |
| 2009/0264932 A1 | 10/2009 | Alamin et al. |
| 2009/0270918 A1 | 10/2009 | Attia et al. |
| 2010/0036424 A1 | 2/2010 | Fielding et al. |
| 2010/0234890 A1 | 9/2010 | Alamin et al. |
| 2010/0234894 A1 | 9/2010 | Alamin et al. |
| 2010/0249839 A1 | 9/2010 | Alamin et al. |

FOREIGN PATENT DOCUMENTS

| | | |
|---|---|---|
| EP | 0 743 045 A2 | 11/1996 |
| EP | 0743045 A3 | 12/1996 |
| EP | 1 994 901 A1 | 11/2008 |
| FR | 2 681 525 A1 | 3/1993 |
| FR | 2 714 591 | 7/1995 |
| FR | 2 717 675 A1 | 9/1995 |
| FR | 2 828 398 A1 | 2/2003 |
| FR | 2 851 154 | 8/2004 |
| FR | 2 884 136 A1 | 10/2006 |
| WO | WO 01/28442 | 4/2001 |
| WO | WO 02/03882 A2 | 1/2002 |
| WO | WO 02/03882 A3 | 5/2002 |
| WO | WO 02/051326 | 7/2002 |
| WO | WO 02/071960 | 9/2002 |
| WO | WO 03/045262 | 6/2003 |
| WO | WO 03/045262 A3 | 1/2004 |
| WO | WO 2004/052246 | 6/2004 |
| WO | WO 2004/073532 | 9/2004 |
| WO | WO 2004/073533 | 9/2004 |
| WO | WO 2005/110258 A1 | 11/2005 |
| WO | WO 2008/051801 | 5/2008 |
| WO | WO 2008/051802 | 5/2008 |
| WO | WO 2008/051802 A3 | 7/2008 |
| WO | WO 2008/051801 A3 | 8/2008 |

OTHER PUBLICATIONS

Chapter 11: Mechanical Aspects of Lumbar Spine in Musculoskeletal Biomechanics., Paul Brinckmann, Wolfgang Frobin, Gunnar Leivseth (Eds.), Georg Thieme Verlag, Stuttgart, 2002; p. 105-128.

Abbott Spine, Wallis Surgical Technique [Product Brochure], 2006; 24 pages total.

Al Baz et al., "Modified Technique of Tension Band Wiring in Flexion Injuries of the Middle and Lower Cervical Spine," Spine, 1995; 20(11): 1241-1244.

Dickman et al., "Comparative Mechanical Properties of Spinal Cable and Wire Fixation Systems," Spine, Mar. 15, 1997; 22(6): 596-604.

Frymoyer et al., "An Overview of the Incidence and Costs of Low Back Pain" Orthrop. Clin. North Am., 1991;22: 263-271.

Garner et al., "Development and Preclinical Testing of a New Tension-Band Device for the Spine: the Loop system," European Spine Journal, 2002; 11 (Suppl 2): S186-191.

Heller, "Stability of Different Wiring Techniques in Segmental Spinal Instrumentation. An Experimental Study," Archives of Orthopedic and Trauma Surgery, Nov. 1997; 117(1-2): 96-99.

Leahy et al., "Design of Spinous Process Hooks for Flexible Fixation of the Lumbar Spine," Proceedings of the Institution of Mechanical Engineers, Part H, Journal of Engineering in Medicine, Sep. 2000; 214( 5):479-487.

Leahy et al., "Mechanical Testing of a Flexible Fixation Device for the Lumbar Spine," Proceedings of the Institution of Mechanical Engineers, Part H: Journal of Engineering in Medicine, Sep. 27, 2000; 214(5): 489-495.

Medtronic Sofamor Danek USA, Inc., DIAM™ System Implant; 2006 [Product Brochure]; downloaded from the Internet: <http://spineinfo.ru/~files/DIAMST.pdf>, 20 pages total.

Minns et al., "Preliminary Design and Experimental Studies of a Novel Soft Implant for Correcting Sagittal Plane Instability in the Lumbar Spine," Spine, Aug. 15, 1997; 22(16): 1819-1825.

Miyasaka et al., "Radiographic Analysis of Lumbar Motion in Relation to Lumbosacral Stability: Investigation of Moderate and Maximum Motion," Spine, Mar. 15, 2000; 25(6): 732-737.

Papp et al., "An In Vitro Study of the Biomechanical Effects of Flexible Stabilization on the Lumbar Spine," Spine, Jan. 15, 1997, 22(2): 151-155.

Shepherd et al., "Spinous Process Strength," Spine, Feb. 1, 2000; 25(3): 319-323.

Shepherd, "Slippage of a Spinous Process Hook During Flexion in a Flexible Fixation System for the Lumbar Spine," Medical Engineering and Physics, Mar. 2001; 23(2): 135-141.

Voydeville et al., "Ligamentoplastie Intervertebrale Avec Cale Souple dans Les Instabilites Lombaries" <<Intervertebral Ligamentoplasty with Flexible Wedge in Lumbar Instability,>>, Orthop Traumatol, vol. 2, 1992, pp. 259-264.

* cited by examiner

METHODS AND APPARATUS FOR LOCKING A BAND

CROSS-REFERENCES TO RELATED APPLICATIONS

The present application is a non-provisional of, and claims the benefit of priority under 35 U.S.C. §119(e) of U.S. Provisional Application No. 61/059,538 filed Jun. 6, 2008, the entire contents of which are incorporated herein by reference.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

1. Field of the Invention

The present invention generally relates to medical methods and apparatus. More particularly, the present invention relates to orthopedic internal fixation such as methods and devices for restricting spinal flexion in patients having back pain or for providing fracture fixation in long bone and trochanteric fractures or other orthopedic applications where a tether may be employed.

A major source of chronic low back pain is discogenic pain, also known as internal disc disruption. Patients suffering from discogenic pain tend to be young, otherwise healthy individuals who present with pain localized to the back. Discogenic pain usually occurs at the discs located at the L4-L5 or L5-S1 junctions of the spine. Pain tends to be exacerbated when patients put their lumbar spines into flexion (i.e. by sitting or bending forward) and relieved when they put their lumbar spines into extension (i.e. by standing or arching backwards). Flexion and extension are known to change the mechanical loading pattern of a lumbar segment. When the segment is in extension, the axial loads borne by the segment are shared by the disc and facet joints (approximately 30% of the load is borne by the facet joints). In flexion, the segmental load is borne almost entirely by the disc. Furthermore, the nucleus shifts posteriorly, changing the loads on the posterior portion of the annulus (which is innervated), likely causing its fibers to be subject to tension and shear forces. Segmental flexion, then, increases both the loads borne by the disc and causes them to be borne in a more painful way. Discogenic pain can be quite disabling, and for some patients, can dramatically affect their ability to work and otherwise enjoy their lives.

Pain experienced by patients with discogenic low back pain can be thought of as flexion instability, and is related to flexion instability manifested in other conditions. The most prevalent of these is spondylolisthesis, a spinal condition in which abnormal segmental translation is exacerbated by segmental flexion. The methods and devices described should as such also be useful for these other spinal disorders or treatments associated with segmental flexion, for which the prevention or control of spinal segmental flexion is desired. Another application for which the methods and devices described herein may be used is in conjunction with a spinal fusion, in order to restrict motion, promote healing, and relieve pain post-operatively. Alternatively, the methods and devices described should also be useful in conjunction with other treatments of the anterior column of the spine, including kyphoplasty, total disc replacement, nucleus augmentation and annular repair. General orthopedic or surgical applications are envisioned where a tether, cable or tape may be employed. An example is trochanteric fracture fixation in which a cerclage device is wrapped around the bone and is attached and tightened to facilitate fracture healing. Similarly, the device may also be used in conjunction with a cerclage device for the fixation of long bone fractures.

Patients with discogenic pain accommodate their syndrome by avoiding positions such as sitting, which cause their painful segment to go into flexion, and preferring positions such as standing, which maintain their painful segment in extension. One approach to reducing discogenic pain involves the use of a lumbar support pillow often seen in office chairs. Biomechanically, the attempted effect of the ubiquitous lumbar support pillow is also to maintain the painful lumbar segment in the less painful extension position.

Current treatment alternatives for patients diagnosed with chronic discogenic pain are quite limited. Many patients follow a conservative treatment path, such as physical therapy, massage, anti-inflammatory and analgesic medications, muscle relaxants, and epidural steroid injections, but typically continue to suffer with a significant degree of pain. Other patients elect to undergo spinal fusion surgery, which commonly requires discectomy (removal of the disk) together with fusion of adjacent vertebra. Fusion may or may not also include instrumentation of the affected spinal segment including, for example, pedicle screws and stabilization rods. Fusion is not usually recommended for discogenic pain because it is irreversible, costly, associated with high morbidity, and has questionable effectiveness. Despite its drawbacks, however, spinal fusion for discogenic pain remains common due to the lack of viable alternatives.

An alternative method, that is not commonly used in practice, but has been approved for use by the United States Food and Drug Administration (FDA), is the application of bone cerclage devices which can encircle the spinous processes or other vertebral elements and thereby create a restraint to motion. Physicians typically apply a tension or elongation to the devices that applies a constant and high force on the anatomy, thereby fixing the segment in one position and allowing effectively no motion. The lack of motion allowed after the application of such devices is thought useful to improve the likelihood of fusion performed concomitantly; if the fusion does not take, these devices will fail through breakage of the device or of the spinous process to which the device is attached. These devices are designed for static applications and are not designed to allow for dynamic elastic resistance to flexion across a range of motion. The purpose of bone cerclage devices and other techniques described above is to almost completely restrict measurable motion of the vertebral segment of interest. This loss of motion at a given segment gives rise to abnormal loading and motion at adjacent segments, which can lead eventually to adjacent segment morbidity.

Another solution involves the use of an elastic structure, such as tethers, coupled to the spinal segment. The elastic structure can relieve pain by increasing passive resistance to flexion while often allowing substantially unrestricted spinal extension. This mimics the mechanical effect of postural accommodations that patients already use to provide relief.

Spinal implants using tether structures are currently commercially available. One such implant couples adjacent vertebrae via their pedicles. This implant includes spacers, tethers and pedicle screws. To install the implant, selected portions of the disc and vertebrae bone are removed. Implants are then placed to couple two adjacent pedicles on each side of the spine. The pedicle screws secure the implants in place. The tether is clamped to the pedicle screws with set-screws, and limits the extension/flexion movements of the vertebrae of interest. Because significant tissue is removed and because of screw placement into the pedicles, the implant and accompanying surgical methods are highly invasive and the implant is often irreversibly implanted. There is also an accompanying high chance of nerve root damage. Where the tip of the set-screw clamps the tethers, the tethers are abraded and may generate particulate debris.

Other implants employing tether structures couple adjacent vertebrae via their processes instead. These implants include a tether and a spacer. To install the implant, the supraspinous ligament is temporarily lifted and displaced. The interspinous ligament between the two adjacent vertebrae of interest is then permanently removed and the spacer is inserted in the interspinous interspace. The tether is then wrapped around the processes of the two adjacent vertebrae, through adjacent interspinous ligaments, and then mechanically secured in place by the spacer or also by a separate component fastened to the spacer. The supraspinous ligament is then restored back to its original position. Such implants and accompanying surgical methods are not without disadvantages. These implants may subject the spinous processes to frequent, high loads during everyday activities, sometimes causing the spinous processes to break or erode. Furthermore, the spacer may put a patient into segmental kyphosis, potentially leading to long-term clinical problems associated with lack of sagittal balance. The process of securing the tethers is often a very complicated maneuver for a surgeon to perform, making the surgery much more invasive. And, as previously mentioned, the removal of the interspinous ligament is permanent. As such, the application of the device is not reversible.

More recently, less invasive spinal implants have been introduced. Like the aforementioned implant, these spinal implants are placed over one or more pairs of spinous processes and provide an elastic restraint to the spreading apart of the spinous processes during flexion. However, spacers are not used and interspinous ligaments are not permanently removed. As such, these implants are less invasive and may be reversibly implanted. The implants typically include a tether and a securing mechanism for the tether. The tether may be made from a flexible polymeric textile such as woven polyester (PET) or polyethylene; multi-strand cable, or other flexible structure. The tether is wrapped around the processes of adjacent vertebrae and then secured by the securing mechanism. The securing mechanism may involve the indexing of the tether and the strap, e.g., the tether and the securing mechanism include discrete interfaces such as teeth, hooks, loops, etc. which interlock the two. Highly forceful clamping may also be used to press and interlock the tether with the securing mechanism. Many known implementations can clamp a tether with the tip of a set-screw, or the threaded portion of a fastener. However, the mechanical forces placed on the spinal implant are unevenly distributed towards the specific portions of the tether and the securing mechanism which interface with each other. These portions are therefore typically more susceptible to abrasion, wear, or other damage, thus reducing the reliability of these spinal implants as a whole. Other known methods use a screw or bolt to draw other components together to generate a clamping force. While these methods may avoid the potentially damaging loads, the mechanical complexity of the assembly is increased by introducing more subcomponents. Other methods use a buckle through which the tether is threaded in a tortuous path, creating sufficient friction to retain the tether. These buckles generally distribute the load over a length of the tether; although they may be cumbersome to use and adjust as the tether is required to be threaded around multiple surfaces and through multiple apertures. Many of the aforementioned methods involve the use of several components, which must often be assembled during the surgical procedure, often within the wound. This adds time, complexity and risk to the surgical procedure.

For the aforementioned reasons, it would be desirable to provide improved methods and apparatus to secure the tethers of such spinal implants together. In particular, such methods and apparatuses should be less invasive and should enable the tether to be more easily, reversibly, repeatably, safely and reliably secured to an implant by a surgeon, in a surgery setting.

2. Description of the Background Art

Patents and published applications of interest include: U.S. Pat. Nos. 3,648,691; 4,643,178; 4,743,260; 4,966,600; 5,011,494; 5,092,866; 5,116,340; 5,180,393; 5,282,863; 5,395,374; 5,415,658; 5,415,661; 5,449,361; 5,456,722; 5,462,542; 5,496,318; 5,540,698; 5,562,737; 5,609,634; 5,628,756; 5,645,599; 5,725,582; 5,902,305; Re. 36,221; U.S. Pat. Nos. 5,928,232; 5,935,133; 5,964,769; 5,989,256; 6,053,921; 6,248,106; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; 7,029,475; 7,163,558; Published U.S. Patent Application Nos. US 2002/0151978; US 2004/0024458; US 2004/0106995; US 2004/0116927; US 2004/0117017; US 2004/0127989; US 2004/0172132; US 2004/0243239; US 2005/0033435; US 2005/0049708; 2005/0192581; 2005/0216017; US 2006/0069447; US 2006/0136060; US 2006/0240533; US 2007/0213829; US 2007/0233096; Published PCT Application Nos. WO 01/28442 A1; WO 02/03882 A2; WO 02/051326 A1; WO 02/071960 A1; WO 03/045262 A1; WO2004/052246 A1; WO 2004/073532 A1; and Published Foreign Application Nos. EP0322334 A1; and FR 2 681 525 A1. The mechanical properties of flexible constraints applied to spinal segments are described in Papp et al. (1997) Spine 22:151-155; Dickman et al. (1997) Spine 22:596-604; and Garner et al. (2002) Eur. Spine J. S186-S191; Al Baz et al. (1995) Spine 20, No. 11, 1241-1244; Heller, (1997) Arch. Orthopedic and Trauma Surgery, 117, No. 1-2:96-99; Leahy et al. (2000) Proc. Inst. Mech. Eng. Part H: J. Eng. Med. 214, No. 5: 489-495; Minns et al., (1997) Spine 22 No. 16:1819-1825; Miyasaka et al. (2000) Spine 25, No. 6: 732-737; Shepherd et al. (2000) Spine 25, No. 3: 319-323; Shepherd (2001) Medical Eng. Phys. 23, No. 2: 135-141; and Voydeville et al (1992) Orthop Traumatol 2:259-264.

BRIEF SUMMARY OF THE INVENTION

The present invention provides fastening mechanisms and methods for releasably locking an implantable surgical tether. Exemplary orthopaedic applications include restricting flexion of at least one spinal segment or securing broken bones together. More particularly, the provided fastening mechanisms and methods relate to improvements to the methods and devices of deploying and implanting spinal implants for the treatment of discogenic pain and other conditions, such as degenerative spondylolisthesis. Specifically, such deployment and implantation methods are made less invasive, easier to operate, and more reliable and reversible by the provided fastening mechanisms and methods.

In a first aspect, the invention provides a surgical fastening mechanism for releasably locking an implantable tether. The mechanism comprises a housing, a roller element, and a locking mechanism. The housing has a central channel therethrough and a first side surface which defines and entry aperture and a second side surface which defines an exit aperture. A side channel extends between the entry and exit apertures. The roller element has a sidewall defining an aperture therethrough. The roller element is slidably disposed at least partially in the central channel such that the entry and exit apertures are at least partially aligned with the roller aperture so as to permit passage of the tether therethrough. The rotation of the roller element in a first direction winds the tether therearound, thereby creating a tortuous or serpentine path in the tether, which generates friction between the roller element, the housing and the tether. The locking mechanism is operably connected with either the housing or the roller element and is adapted to prevent rotation of the roller within the central channel of the housing and also adapted to prevent release of the tether from the roller. The tortuous path created does not result in deformation of the strap within the plane of the strap.

In various embodiments, the roller element may further include various features. The roller element may be rotationally disposed in the central channel or threadably engaged with the housing. Threads on either the roller element or the housing may further be partially deformed, thereby further securing the roller element with the housing. The roller element may rotationally lock the tether in position relative to the housing. The roller element may comprise a driver feature. The driver feature is adapted to receive a tool to permit rotation of the roller element. The driver element may be, for example, a Phillips head, a slotted flat head, a Torx head, or a hex head. The roller element may have a variety of shapes. For example, it may be substantially cylindrically shaped or eccentrically shaped. The fastening mechanism further may comprise a pin coupled with the housing and the roller element may comprise a groove adapted to receive the pin, thereby locking the roller element with the housing. The roller element may comprise an alignment feature that is adapted to limit rotation of the roller relative to the housing. The housing may comprise a flange adapted to retain the roller and/or locking elements. The roller element may comprise an alignment feature adapted to align the roller aperture with the first and second side apertures in the housing. The alignment feature may be, for example, a pin or a shoulder. The alignment feature may also be a feature of the housing that limits travel of the roller. Although the purpose of the alignment feature is to constrain rotation of the roller, it may directly limit translation of the roller along its axis, for example when the roller element is threadably engaged with the housing. If the roller is threadably engaged with the housing, rotation of the roller will also result in translation due to the threads. Therefore directly constraining translation of the roller, e.g. with a flange or other surface, the rotation of the roller will also be constrained. This system may present advantages for fabrication.

In some embodiments, the locking mechanism comprises a set screw threadably engaged with the housing. Threads on either the locking member or the housing may be partially deformed, thereby further securing the locking mechanism with the housing. The set screw may be engaged against the roller element. The set screw may comprise a driver feature adapted to receive a tool to permit rotation of the set screw. The driver feature may be, for example, a Phillips head, a slotted flat head, a Torx head, or a hex head. The driver feature on the set screw may comprise an aperture large enough to permit access to the roller element with a tool for rotation thereof while the set screw is threadably engaged with the housing. The locking mechanism may be frictionally engaged with the roller and/or the housing. The locking mechanism may be captively retained, along with the roller, within the housing by a feature such as a flange such that the entire fastening mechanism is an inseparable assembly. The flange may be welded or press-fit to create this inseparability. In other embodiments, the locking mechanism may comprise a friction fit between the roller element and the housing. In preferred embodiments, the housing, the roller element and the locking mechanism are held together and are inseparable from one another while the fastening mechanism is undamaged.

In some embodiments, the fastening mechanism may comprise a pin coupled with the housing. The locking mechanism comprises a groove adapted to receive the pin, thereby locking the locking mechanism with the housing. In other embodiments, a rotation limiting element such as a pin or shoulder is coupled with the housing and the locking mechanism has a receiver for receiving the rotation locking element, thereby limiting rotation of the locking mechanism relative to the housing. As for the roller, the rotation of the locking element may be constrained by limiting translation of the locking element along its axis. By limiting translation of a threaded locking element, rotation of the element may also be limited. The locking and roller elements may be in series with each other, such that constraining translation and/or rotation of the locking element thereby constrains translation and/or rotation of the roller element such that at the limits of rotation of the roller element, the aperture through the roller is aligned with the entry and exit apertures of the housing. This facilitates direct insertion of the tether through these apertures.

In still other embodiments, the housing may include various features. The housing may comprise a flange adapted to retain the locking element. The entry and exit apertures of the housing may be shaped like rectangular slots. The housing may comprise an alignment feature such as a pin or shoulder coupled with either the housing or the roller element, adapted to align the roller aperture with the entry and exit apertures in the housing. The entry and exit apertures may be also be referred to as first and second side apertures, respectively. The housing may have third and fourth outer surfaces and the central channel may extend from the third outer surface to the fourth outer surface.

The fastening mechanism may be configured so that the rotation of the roller element may serve a variety of purposes. The roller element may be rotated approximately 180 degrees in order to create the friction interface. In other embodiments, the roller element is adapted to be rotated a selected amount so as to retract a desired length of the tether into the housing. The selected amount may range from about ¼ turn to about two full revolutions of the roller element. The rotation of the roller element may create a tortuous path for the tether as it passes between the first and second side apertures. The rotation of the roller may lock the tether so as to fix the tether's position relative to the housing. The rotation of the roller may retract both a working end and a tail end of the tether inward toward the roller. This may retract an equal or different length of the tether's working end compared to that of the tail end. The size of the roller may be designed such that a specific, desired length of the tether is retracted. The rotation of the roller element in a second direction opposite of the first direction may unwind the tether therefrom, thereby reducing the friction fit between the tether and the fastening mechanism. The roller may be rotated by a variable amount so that the length of tether that is retracted is controlled by the operator. This further enhances the continuous adjustability of the attachment mechanism.

In many embodiments, the fastening mechanism may further comprise a position indicator adapted to provide visual, tactile or audible feedback to an operator on the relative position of the roller with respect to the housing. The position indicator may comprise detents or calibration marks on either the housing or the roller element and they may be radiopaque to permit visualization under x-ray, fluoroscopy or other radiographic methods.

Preferably, the tether remains undeformed along planes in which the tether lies and the tether is only deformed along a plane that lies transverse to planes in which the tether lies such that any curvature of the strap is around an axis parallel to the axis of the roller, such that the tether is not required to be twisted or bent. The tether often may comprise a spinous process constraint device that is adapted to limit flexion between adjacent spinous processes or between a spinous process and a sacrum. The tether may also be used for other surgical applications such as to hold two or more anatomic structures together, e.g. holding a fractured bone together.

In another aspect, the invention provides a method for releasably locking an implantable tether. The tether is advanced through an aperture in a housing and through an aperture in a roller element. The tether may be advanced through the housing and the roller element in a single linear motion. The roller element is at least partially disposed in the housing. The roller element is rotated in a first direction so as to retract the tether into the housing, thereby forming the tether into a tortuous path and creating sufficient friction between the roller element and the housing to retain the tether. The roller element is releasably locked in position relative to the housing.

In various embodiments, the provided method may further comprise various steps and/or features. The roller may be threadably engaged with the housing. Rotating the roller in a first direction may comprise rotating the roller approximately 180 degrees, may lock the tether in position relative to the housing, may comprise rotating a tool engaged with the roller element, and/or may retract both a working end and a tail end of the tether inward toward the roller. Rotating the roller may also simultaneously lock the roller. Rotating the roller may comprise rotating the roller a selected amount so as to retract a desired length of the tether into the housing. The selected amount may range from about ¼ turn to about two full revolutions of the roller element. Releasably locking the roller element may comprise placing a pin in the housing, or it may comprise threadably engaging a set screw with the housing. It may also comprise threadably engaging the roller element with the housing, or it may comprise manually overcoming a static friction between the roller and housing. Releasably locking the roller element may comprise pressing the roller element into the housing thereby creating a friction fit. Longitudinal movement of the roller element in a central channel of the housing may be constrained so as to also limit rotation of a threaded roller element.

In some embodiments, the roller may be externally controllable by a controller such as a radiofrequency transcutaneous transmitter. This allows the patient or physician to adjust the tether and fine tune the implant without requiring additional surgery. Thus a patient may easily adjust the tether to accommodate for different physical activities, body positions and other factors that affect lower back pain.

The provided method may further comprise additional steps. The housing aperture may be aligned with the roller aperture to permit advancement of the tether therethrough. The roller element may be rotated in a second direction opposite the first direction, thereby unwinding the tether from the roller element and reducing the friction fit between the roller element and the housing. A position indicator may be monitored. The indicator indicates the relative position of the roller with respect to the housing. All components of the mechanism may be captively retained within the housing, creating an inseparable assembly.

These and other embodiments are described in further detail in the following description related to the appended drawing figures.

DETAILED DESCRIPTION OF THE INVENTION

Figure 1:
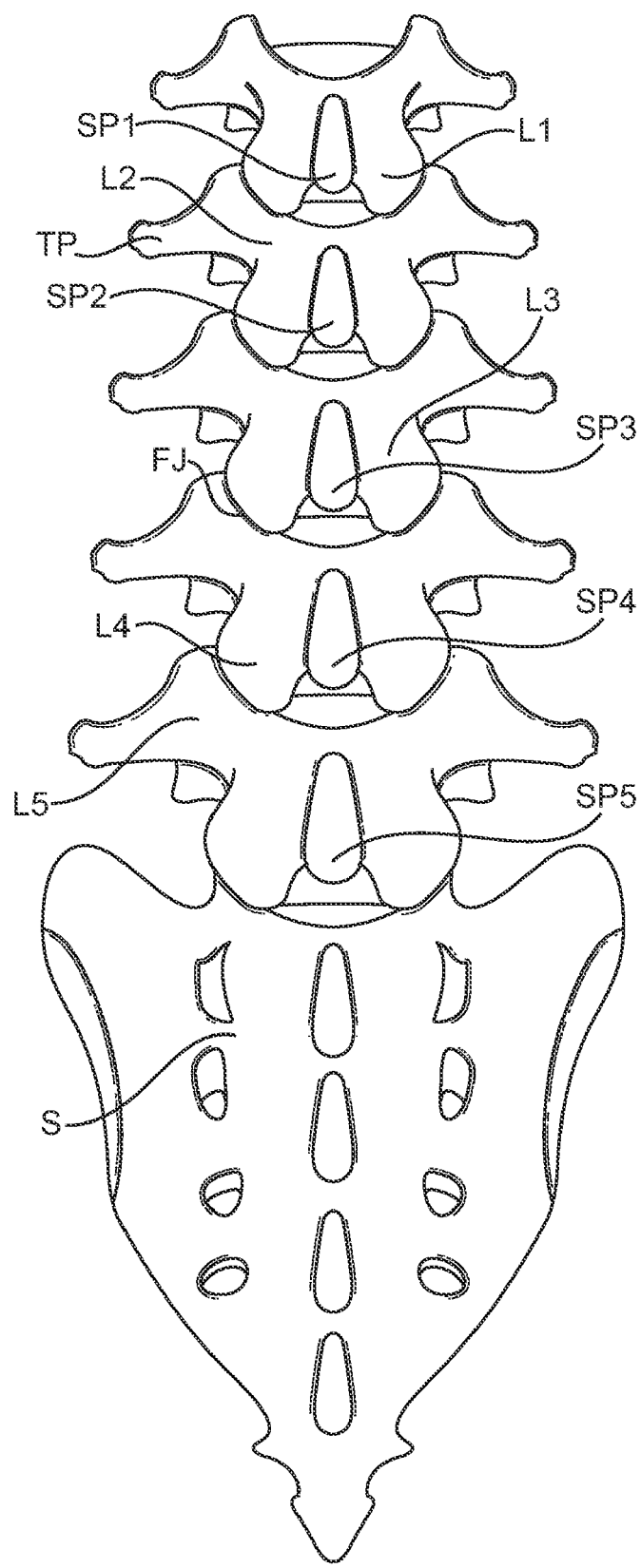
FIG. 1 is a schematic diagram illustrating the lumbar region of the spine.
Figure 1A:
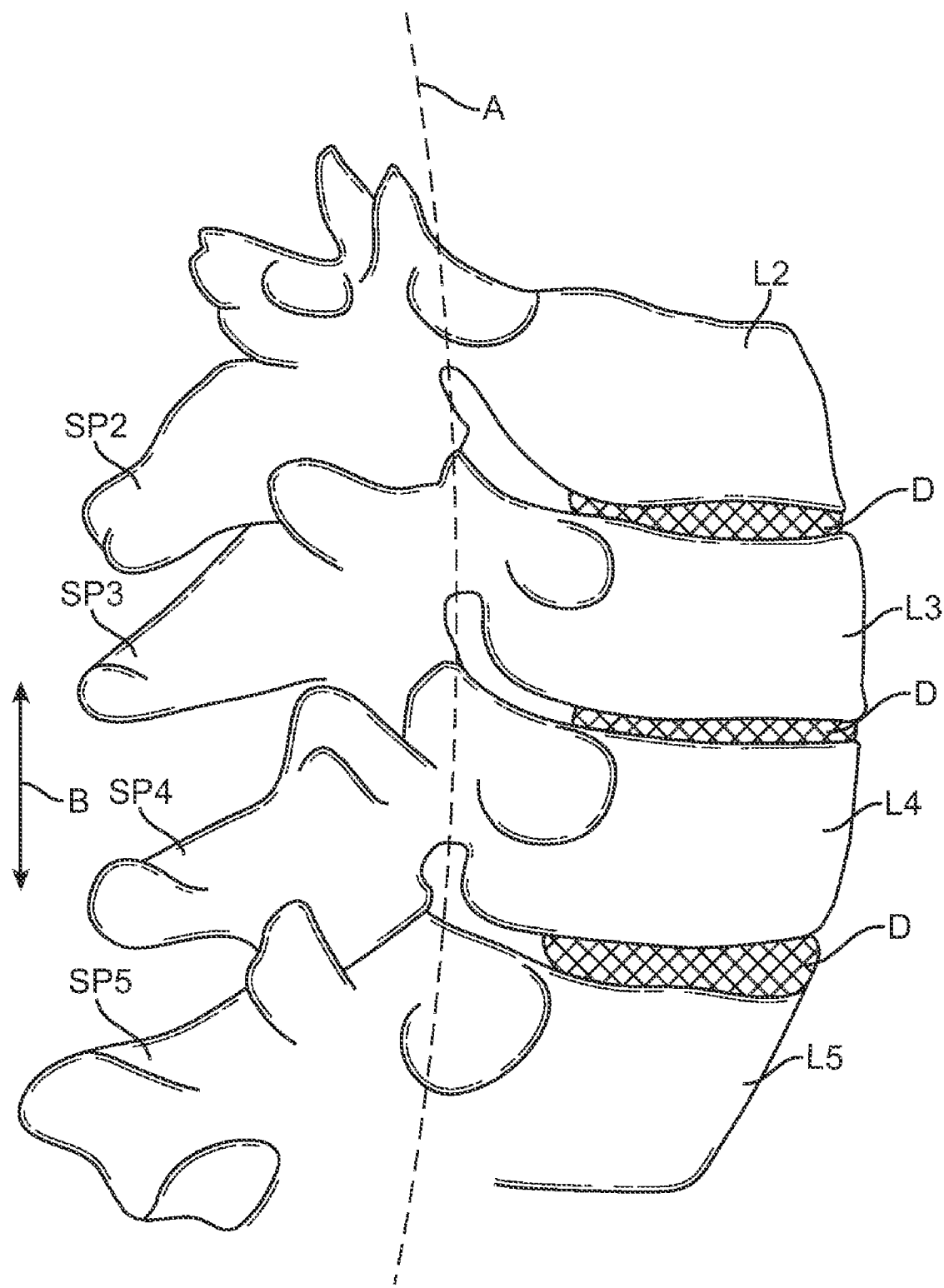
FIG. 1A a schematic illustration showing a portion of the lumbar region of the spine taken along a sagittal plane.

FIG. 1 is a schematic diagram illustrating the lumbar region of the spine including the spinous processes (SP), facet joints (FJ), lamina (L), transverse processes (TP), and sacrum (S). FIG. 1A is a schematic illustration showing a portion of the lumbar region of the spine taken along a sagittal plane and is useful for defining the terms "neutral position," "flexion," and "extension" that are often used in this disclosure.

As used herein, "neutral position" refers to the position in which the patient's spine rests in a relaxed standing position. The "neutral position" will vary from patient to patient. Usually, such a neutral position will be characterized by a slight curvature or lordosis of the spine where the spine has a slight anterior convexity and slight posterior concavity. In some cases, the presence of the constraint of the present invention may modify the neutral position, e.g. the device may apply an initial force which defines a "new" neutral position having some extension of the untreated spine. As such, the use of the term "neutral position" is to be taken in context of the presence or absence of the device. As used herein, "neutral position of the spinal segment" refers to the position of a spinal segment when the spine is in the neutral position.

Furthermore, as used herein, "flexion" refers to the motion between adjacent vertebrae in a spinal segment as the patient bends forward. Referring to FIG. 1A, as a patient bends forward from the neutral position of the spine, i.e. to the right relative to a curved axis A, the distance between individual vertebrae L on the anterior side decreases so that the anterior portion of the intervertebral disks D are compressed. In contrast, the individual spinous processes SP on the posterior side move apart in the direction indicated by arrow B. Flexion thus refers to the relative movement between adjacent vertebrae as the patient bends forward from the neutral position illustrated in FIG. 1A.

Additionally, as used herein, "extension" refers to the motion of the individual vertebrae L as the patient bends backward and the spine extends from the neutral position illustrated in FIG. 1A. As the patient bends backward, the anterior ends of the individual vertebrae will move apart. The individual spinous processes SP on adjacent vertebrae will move closer together in a direction opposite to that indicated by arrow B.

Figure 2:
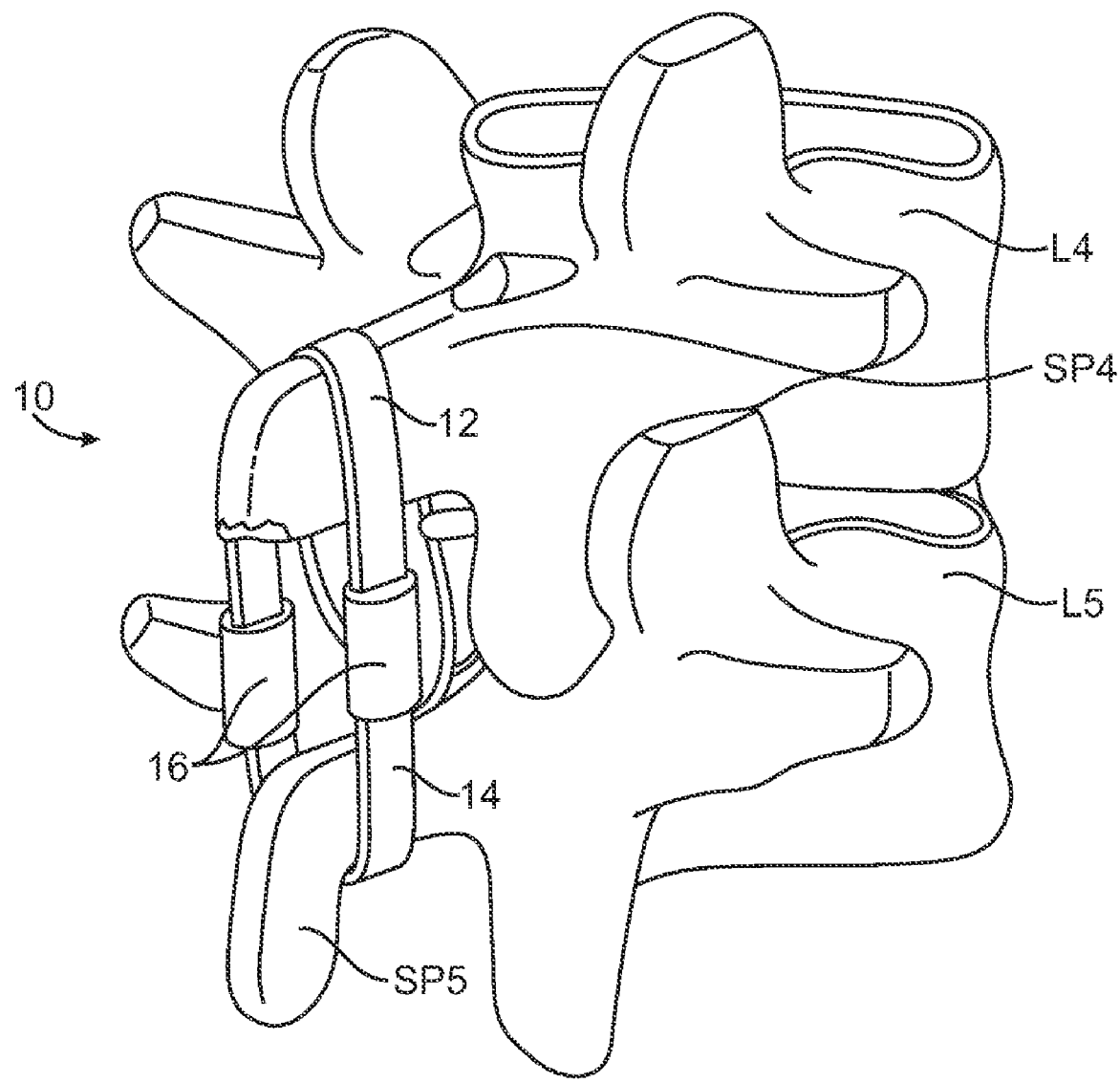
FIG. 2 illustrates a spinal implant of the type described in US 2005/0216017A1.

FIG. 2 shows a spinal implant of the type described in related U.S. Patent Publication No. 2005/0216017 A1 (now U.S. Pat. No. 7,458,981), the contents of which are herein incorporated by reference. As illustrated in FIG. 2, an implant 10 typically comprises an upper strap component 12 and a lower strap component 14 joined by a pair of compliance members 16. The upper strap 12 is shown disposed over the top of the spinous process SP4 of L4 while the lower strap 14 is shown extending over the bottom of the spinous process SP5 of L5. The compliance member 16 will typically include an internal element, such as a spring or rubber block, which is attached to the straps 12 and 14 in such a way that the straps may be "elastically" or "compliantly" pulled apart as the spinous processes SP4 and SP5 move apart during flexion. In this way, the implant provides an elastic tension on the spinous processes which provides a force that resists flexion. The force increases as the processes move further apart. Usually, the straps themselves will be essentially non-compliant so that the degree of elasticity or compliance may be controlled and provided solely by the compliance members 16.

Figure 3A:
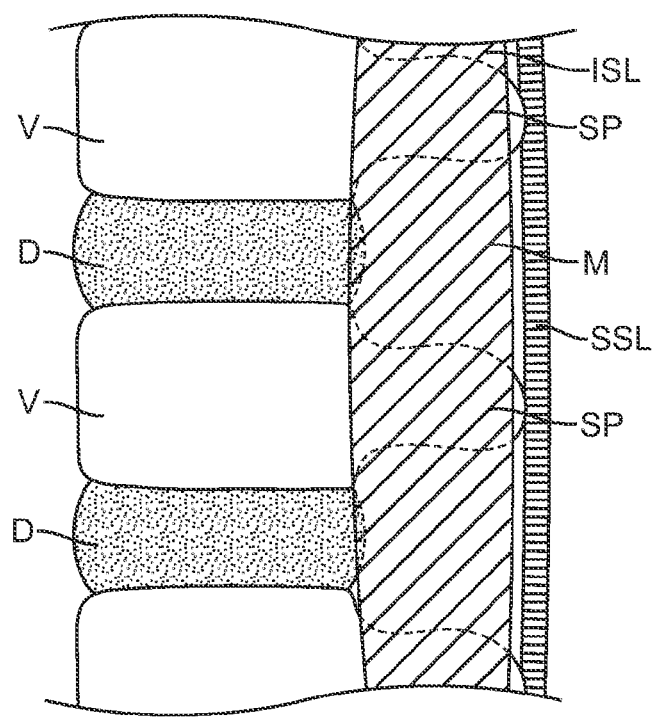
FIGS. 3A-3B illustrate additional tissue surrounding the spinous processes.
Figure 3B:
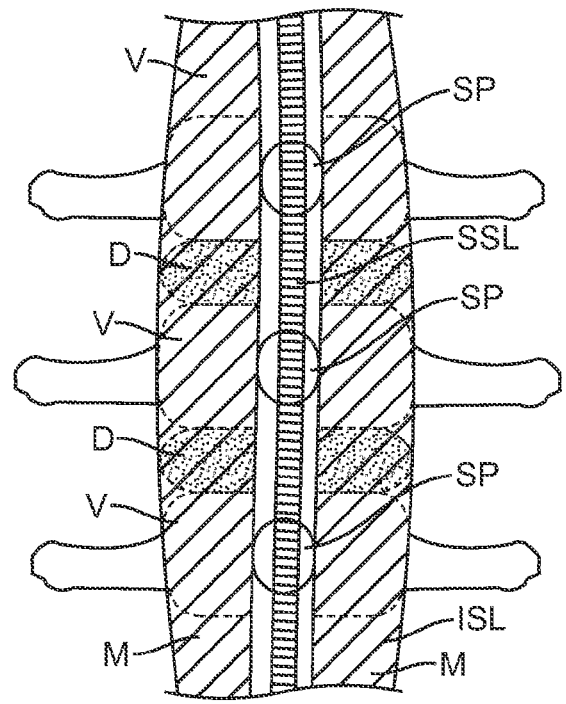

FIG. 3A is a side view of the lumbar region of the spine having discs D separating the vertebral bodies V. The supraspinous ligament SSL runs along the posterior portion of the spinous processes SP and the interspinous ligament ISL and multifidus tendon and muscle M run alongside of and attach to the spinous processes SP. FIG. 3B is a posterior view of FIG. 3A.

Figure 4A:
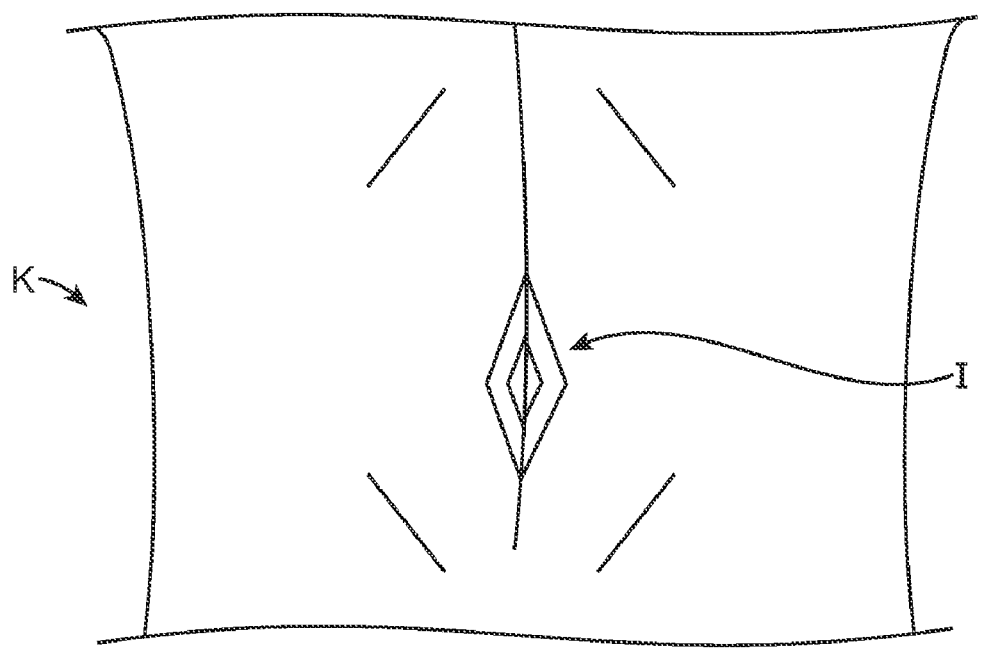
FIGS. 4A-4M show an exemplary method of surgically implanting a spinal device.
Figure 4B:
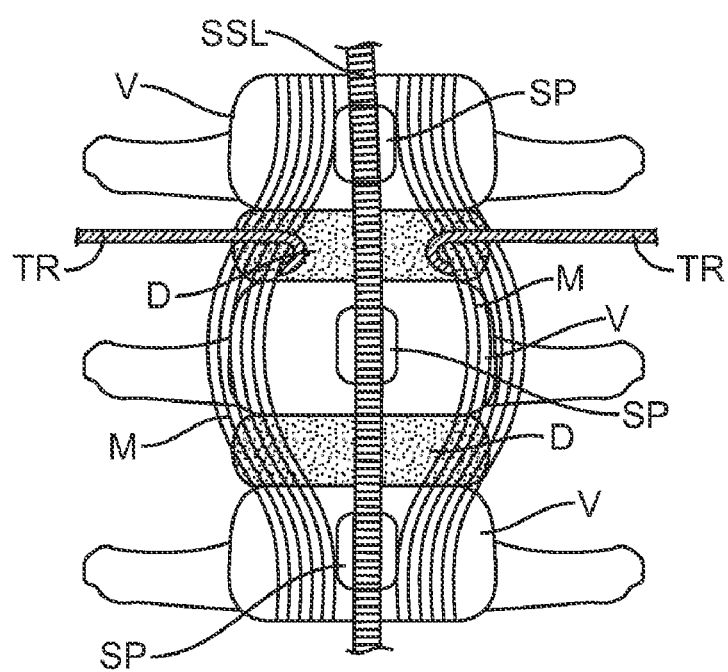

FIGS. 4A-4M illustrate an exemplary surgical method of implanting a spinous process constraint such as the embodiment of FIG. 2. One of the first steps to surgically implant a spinal implant is to make an incision to access the spinal area of interest. FIG. 4A shows the lumbar region of back K after an incision I has been made through the patient's skin. FIG. 4B illustrates the lumbar region of the spine after the incision I has been made through the patient's skin. Multifidus muscle and tendon M have been retracted with retraction tools TR to expose the spinous processes.

Figure 4D:
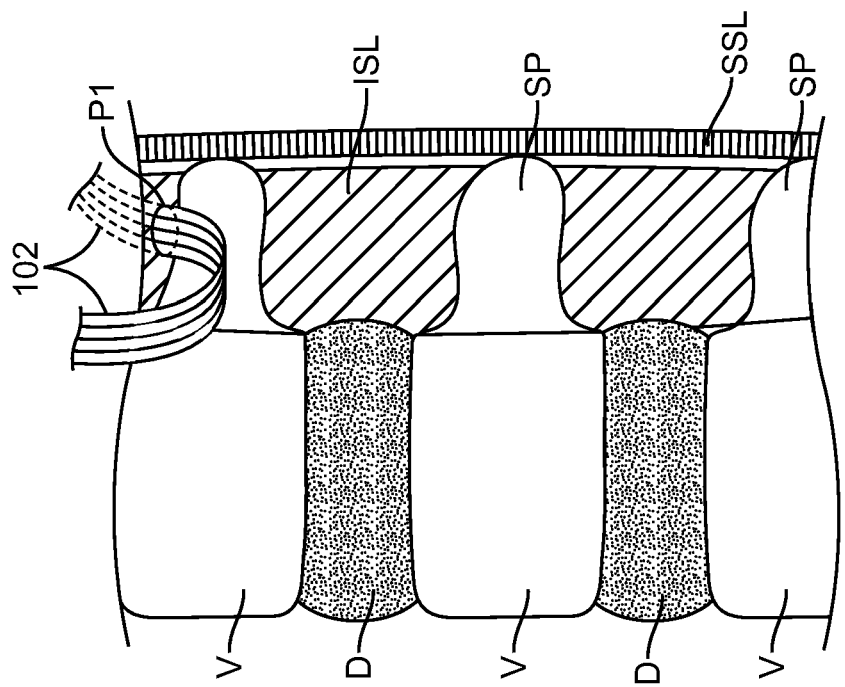
Figure 4C:
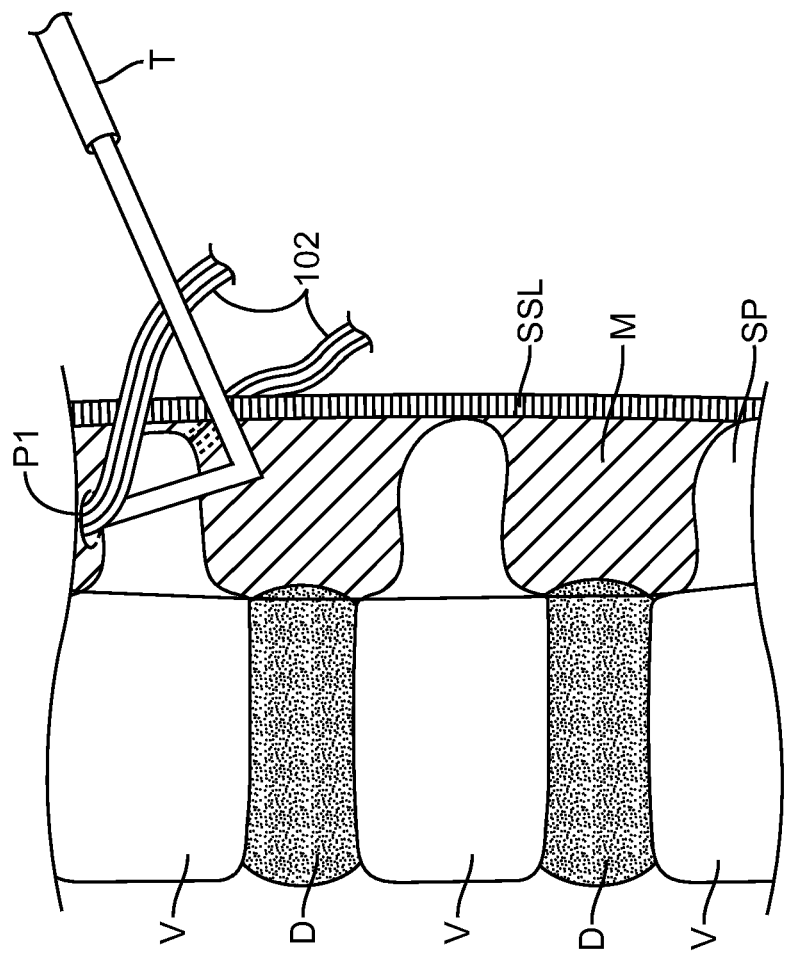

After the incision has been made, a piercing tool T having a sharp distal end may be used to access and pierce the interspinous ligament ISL while avoiding the supra spinous ligament SSL, creating an interspinous ligament perforation P1 superior of the first spinous process SSP of interest. This surgical approach is desirable since it keeps the supra spinous ligament intact and minimizes damage to the multifidus muscle and tendons and other collateral ligaments. As shown in FIG. 4C, from the right side of the spine, tool T accesses and pierces the interspinous ligament ISL adjacent of the first spinous process SSP of interest. The distal end of tool T is shown in dotted line. Alternatively, tool T may access and pierce the interspinous ligament ISL from the left side instead. The distal end of tool T is coupled with tether 102, parts of which are also shown in dotted line. In addition to accessing and piercing the interspinous ligament ISL, piercing tool T also advances or threads tether 102 through perforation P1. As shown in FIG. 4D, tool T is then removed, leaving tether 102 positioned through perforation P1. Multifidus tendon and muscle M is not shown in FIGS. 4C and 4D so that other elements are shown more clearly.

Figure 4E:
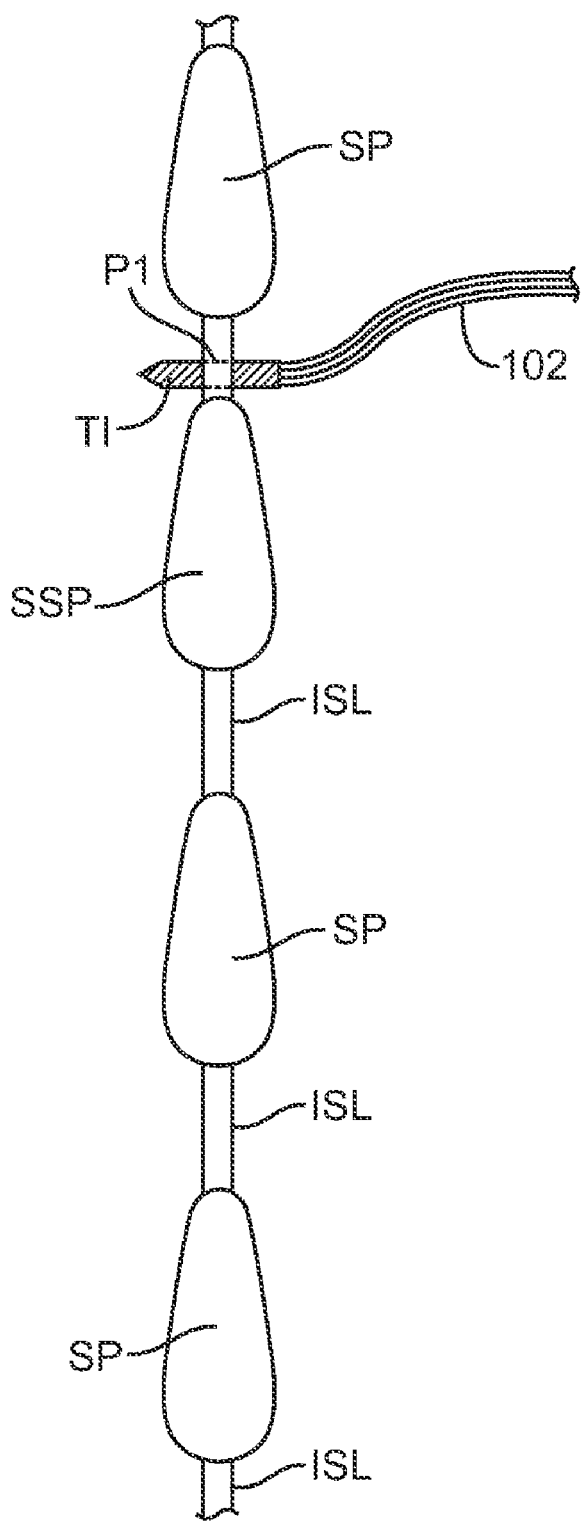

FIG. 4E is a posterior view of a section of the spine after the above steps have been performed. Often times, the distal tip TI of tool T is detachable. As shown in FIG. 4E, after tool T accesses and pierces the interspinous ligament ISL with distal tip TI, distal tip TI is detached from tool T and is left in place in perforation P1 (shown in dotted line) above the first spinous process SSP of interest. Tether 102 lags behind tip TI. In some cases, distal tip TI may fully pierce through interspinous ligament ISL. In these cases, distal tip TI has passed through the interspinous ligament ISL while a portion of tether 102 is left in place in perforation P1.

Figure 4F:
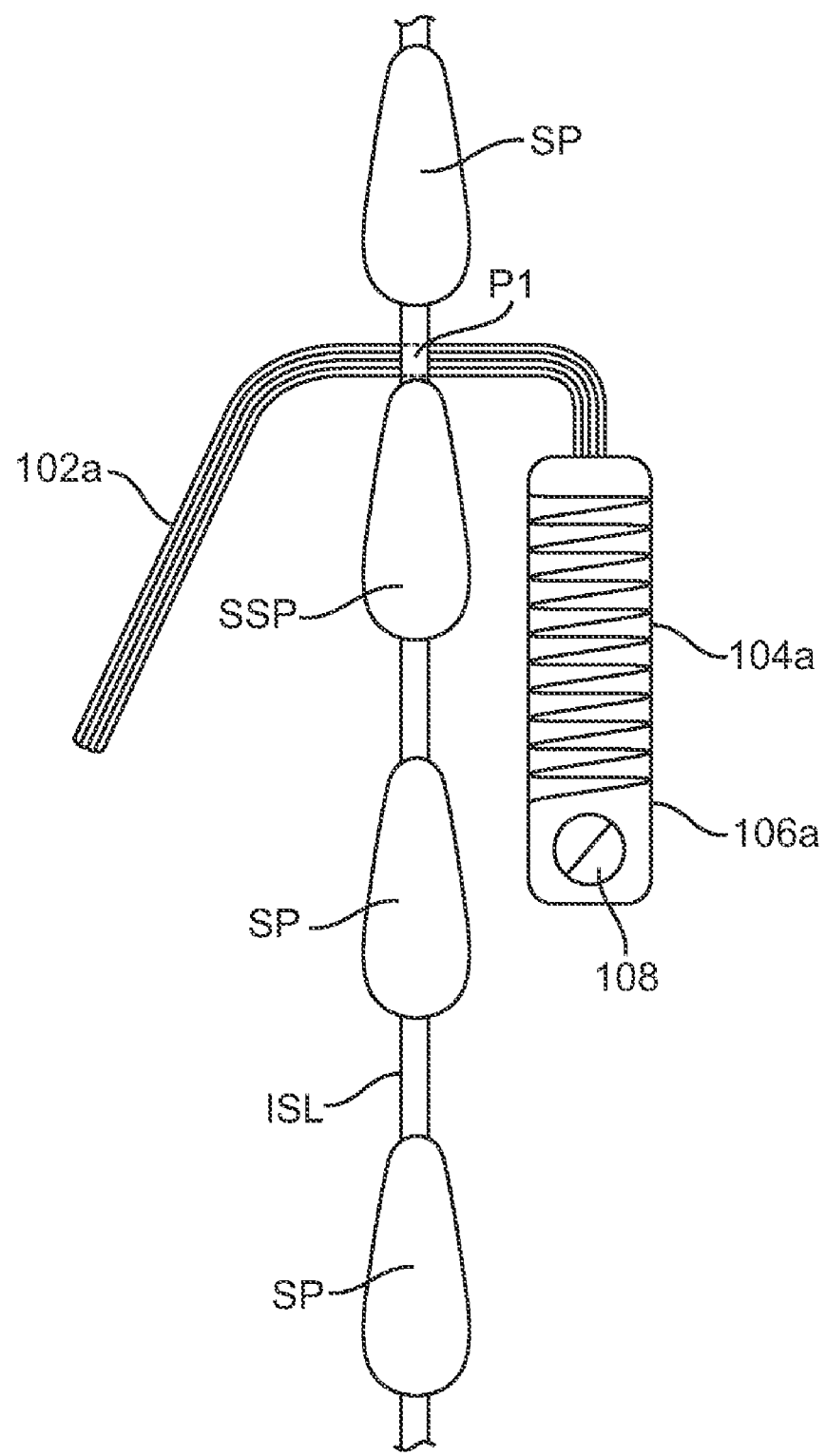

After tip TI or a portion of tether TH is left in place in perforation P1, another tool may couple with tip TI and pull tip TI such that it drags tether 102a and compliance element 104a to its appropriate position relative to the spine, as shown in FIG. 4F. Compliance element 104a is coupled to tether 102a and is used to provide a force resistive to flexion of spinous processes SP. Compliance element 104a includes a fastening mechanism or fastening element 106a and may further comprise a spring, a tensioning member, a compression member, or the like. Related compliance members are described in commonly owned U.S. patent application Ser. No. 12/106,103, the entire contents of which are incorporated herein by reference.

Figure 4H:
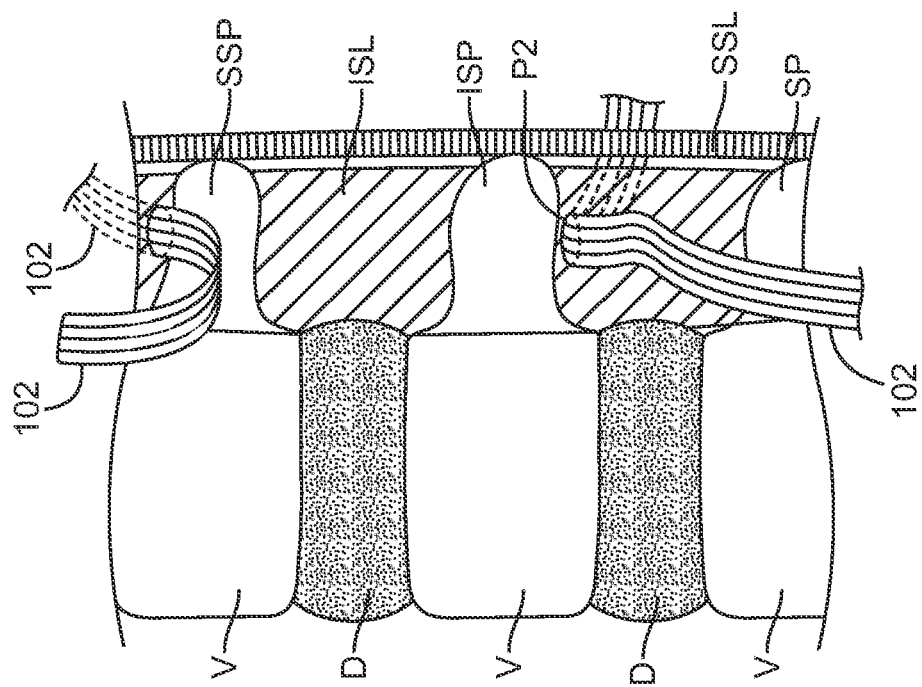
Figure 4G:
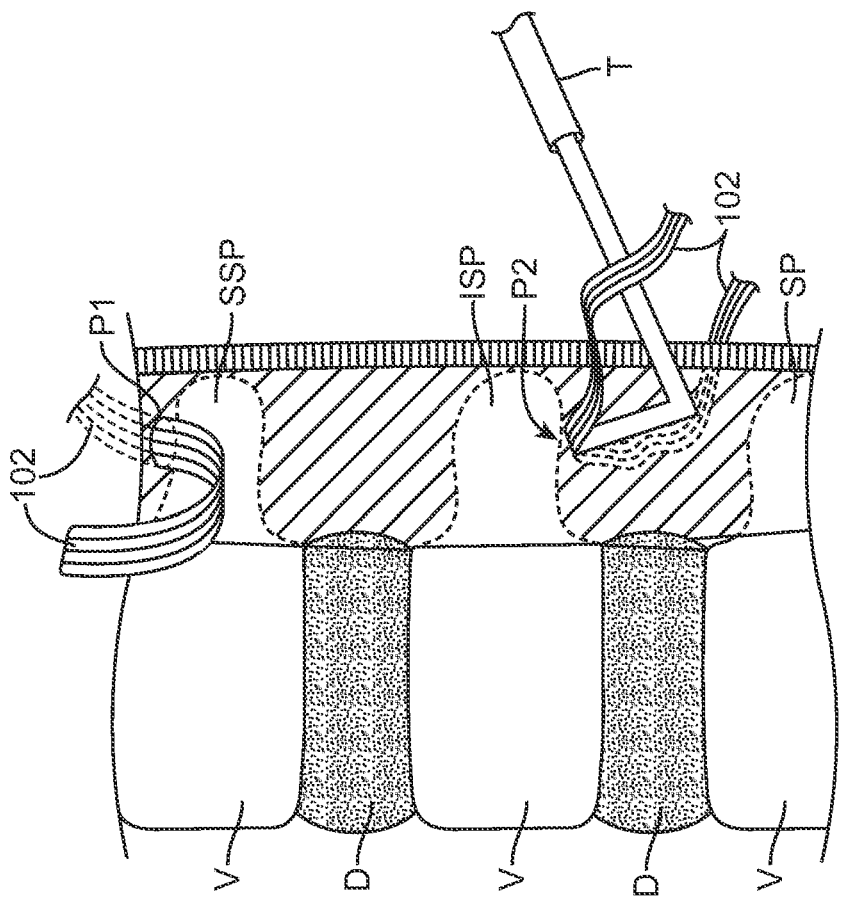

The steps of accessing the ISL, piercing the ISL, and threading tether 102 through a perforation are then repeated for the opposite, lateral side of the spine for an adjacent spinous process ISP, inferior of the first superior spinal process SSP of interest. As shown in FIGS. 4G and 4H, tool T accesses the interspinous ligament from the left side of the spinal midline and pierces the interspinous ligament ISL, creating a second perforation P2 located inferior of a second spinous process of interest, labeled as inferior spinous process ISP. As shown in FIG. 4G, the inferior spinous process ISP of interest is directly adjacent to and inferior of the first superior spinous process SSP of interest. However, it is entirely possible to perform the described procedure starting with the inferior spinous process ISP first instead of the superior spinous process SSP, for example, perforation P2 may be created before perforation P1. It is also possible that there may be a gap of one or more spinous processes SP between the spinous processes of interest. Multifidus tendon and muscle M is not shown in FIGS. 4G and 4H for clarity of the other shown elements.

Figure 4I:
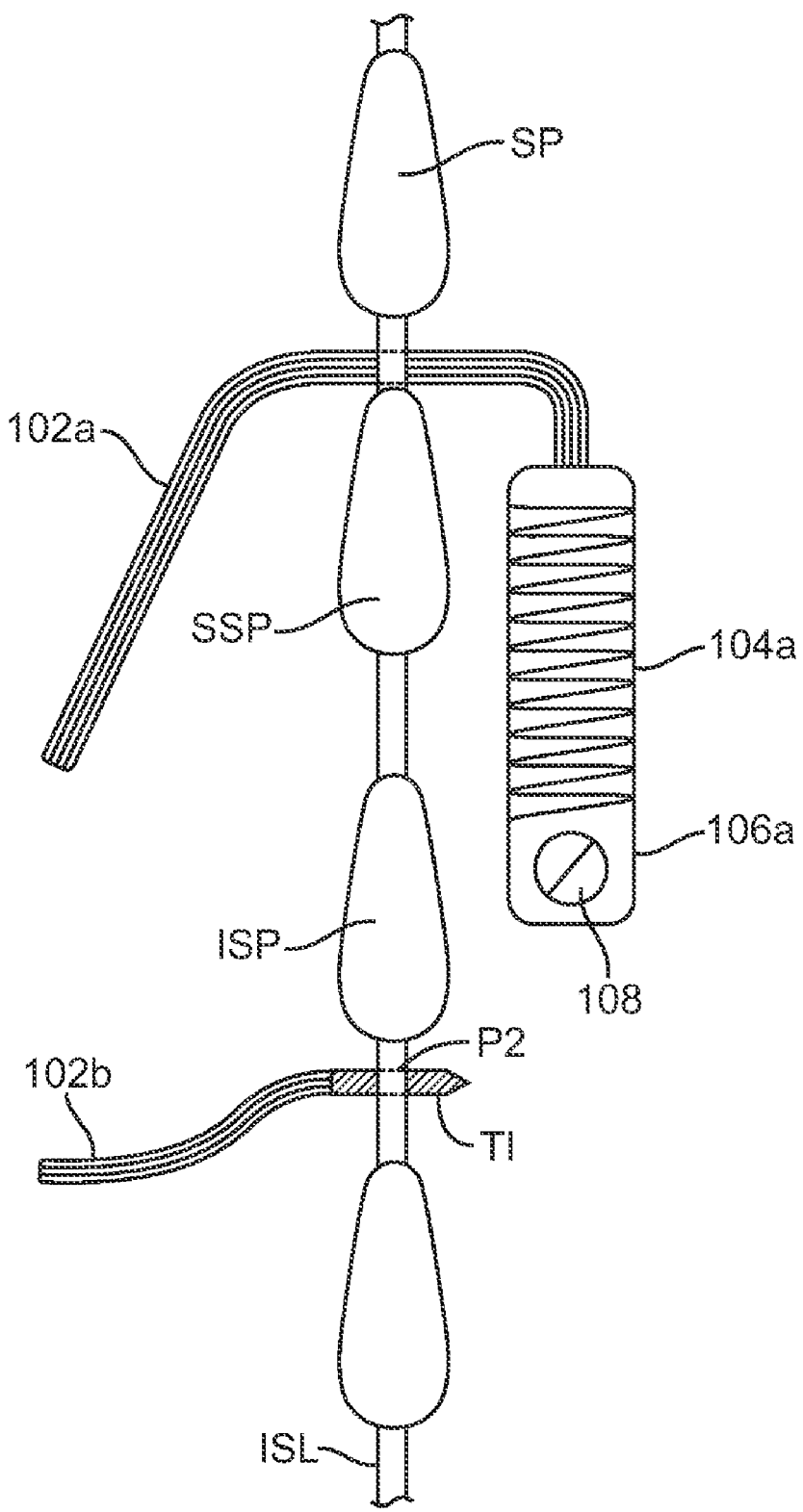
Figure 4J:
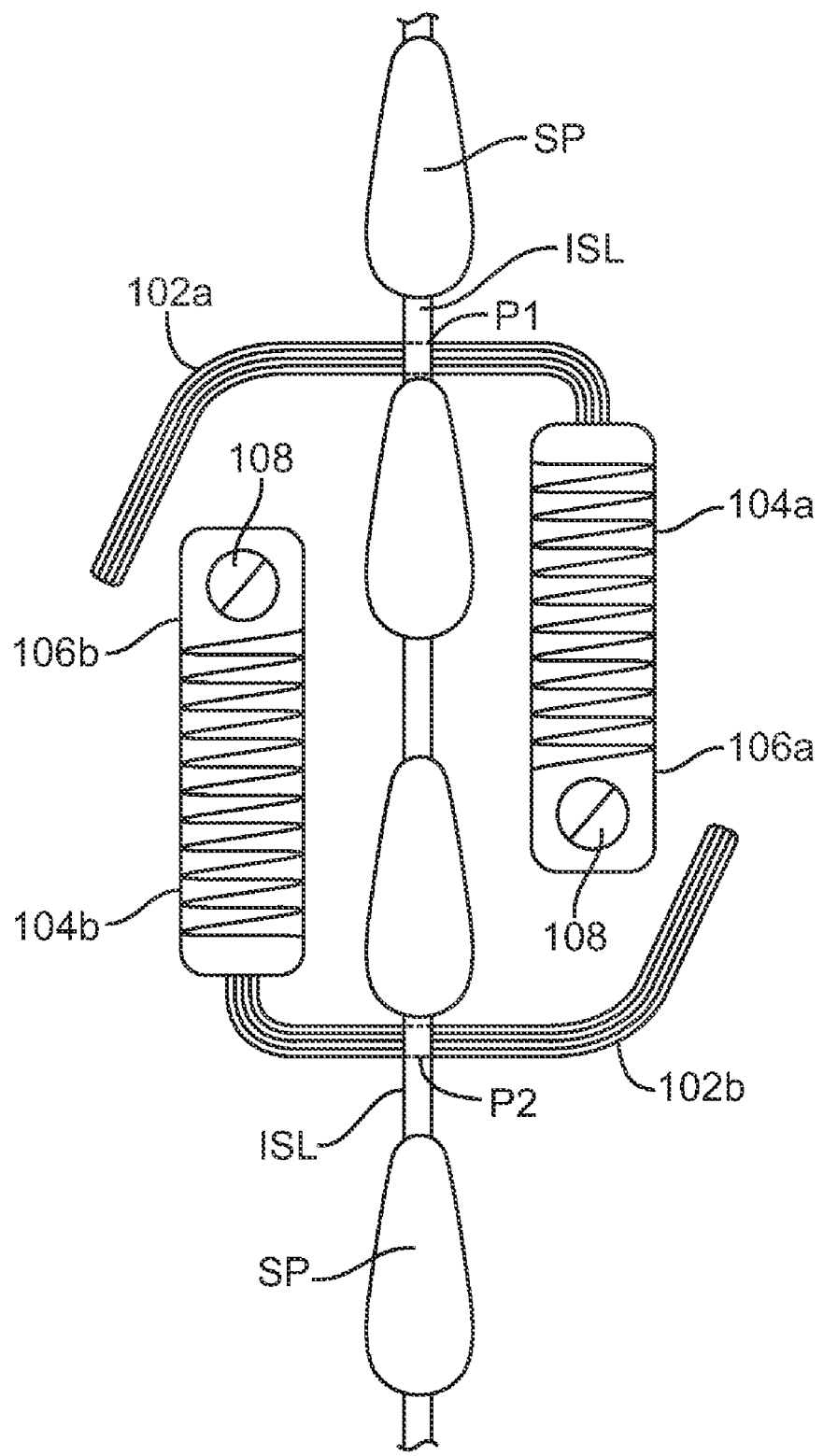
Figure 4K:
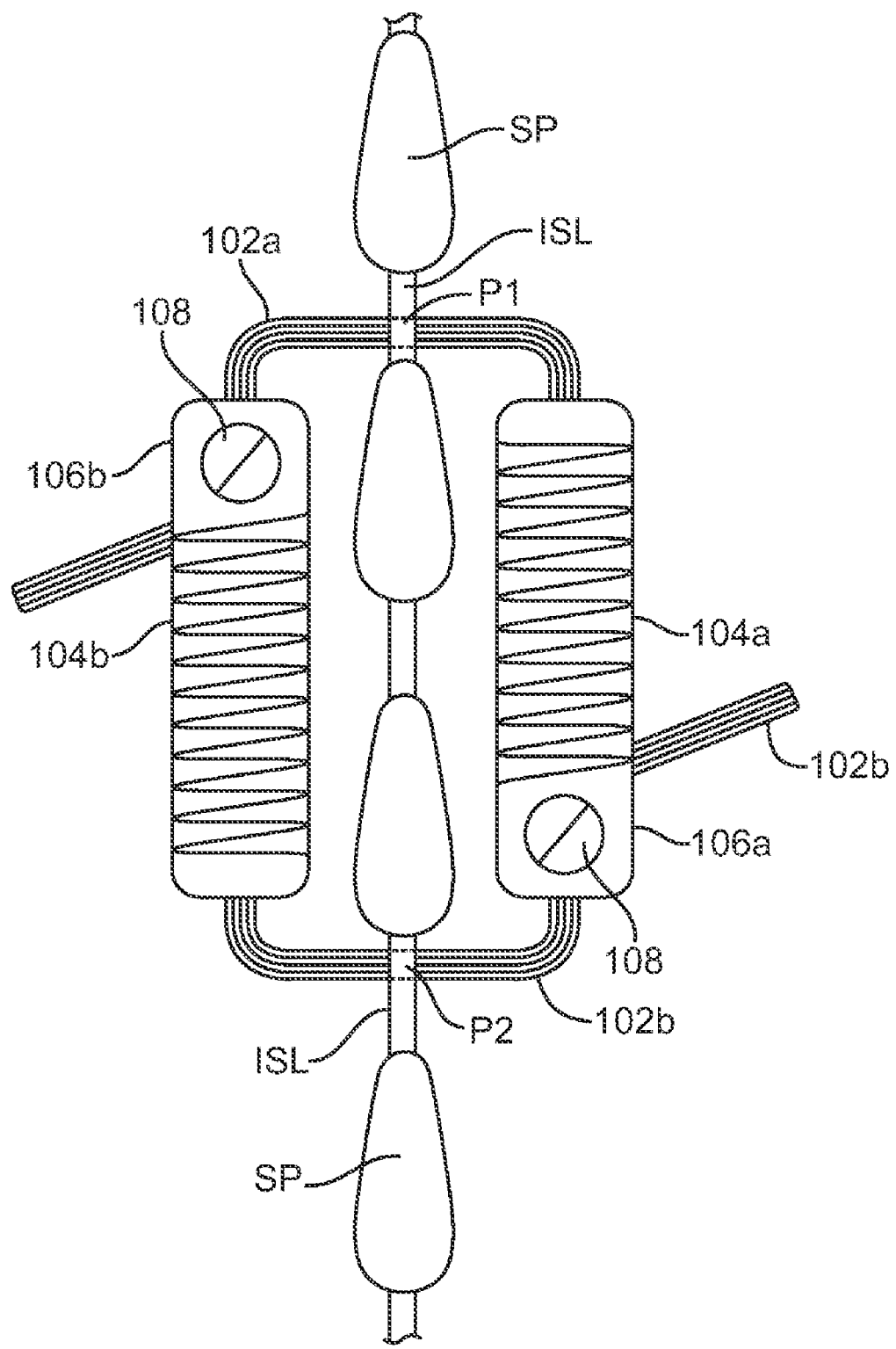

As shown in FIGS. 4H, 4I and 4J, like with the steps shown in conjunction with the first piercing, tether 102b is pierced through perforation P2 and left in place along with distal tip TI of tool T (best seen in FIG. 4I). Another tool such as a pair of forceps, is then used to grasp distal tip TI to pull tether 102b and compliance element 104b in place relative to the spine, as shown in FIG. 4J. Opposing compliance members 104a and 104b on opposite sides of spinous processes SP are oriented in opposite directions. Each compliance element 104a, 104b is coupled with their respective tether 102a, 102b and has a respective fastening mechanism or fastening element 106a, 106b. Fastening mechanism 106a, 106b are configured to couple with the tether 102a, 102b of the opposing compliance member 104a, 104b. For example as shown in FIG. 4K, tether 102a is advanced through compliance member 104b and is coupled with fastening mechanism 106b while tether 102b is advanced through compliance member 104a and is coupled with fastening mechanism 106a. Except for their orientation, compliance members 104a and 104b are identical. One of skill in the art will appreciate that the tether may enter and exit the fastening mechanism in a number of different directions and configurations, and FIG. 4K merely is one exemplary embodiment.

Figure 4L:
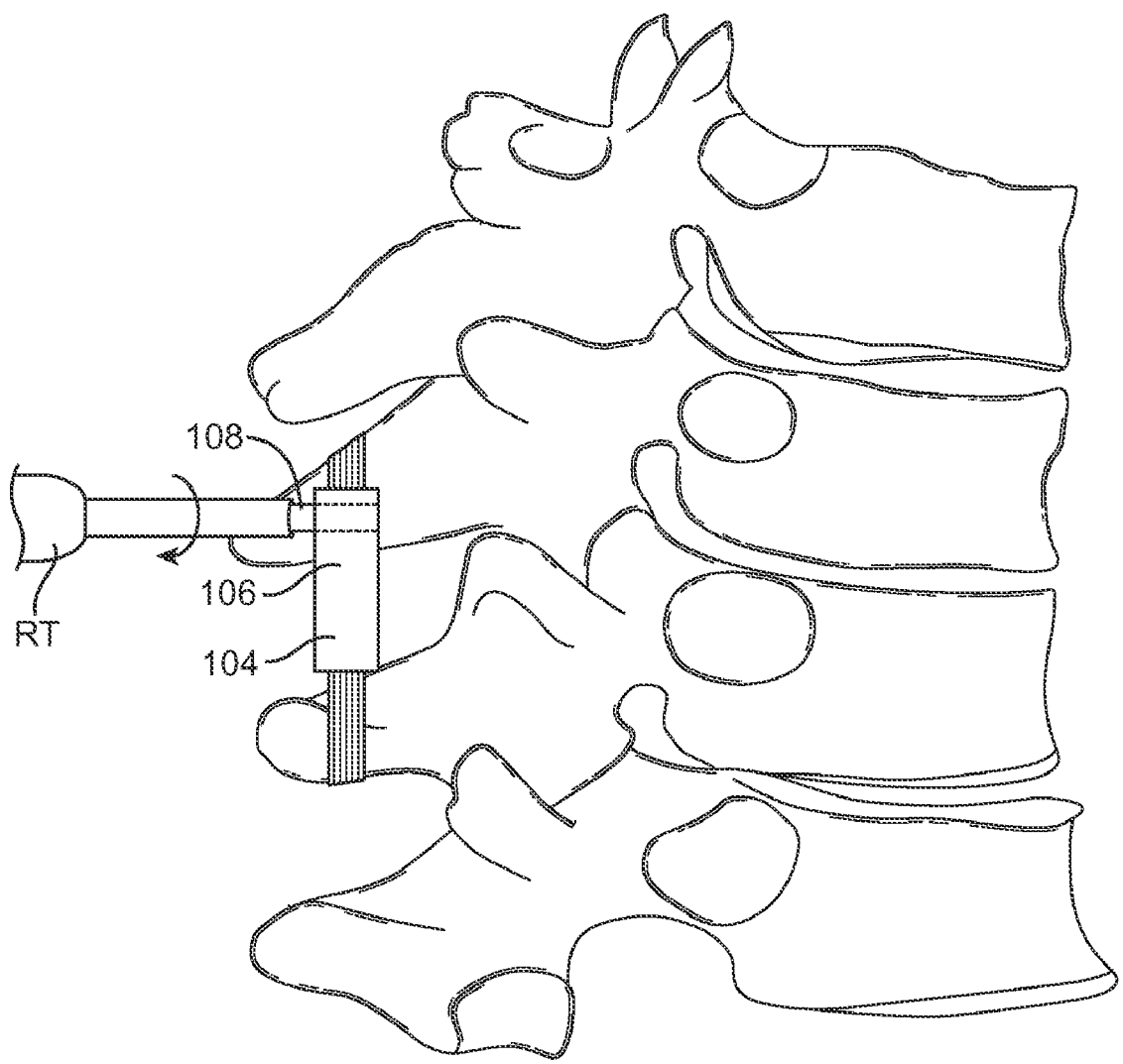
Figure 4M:
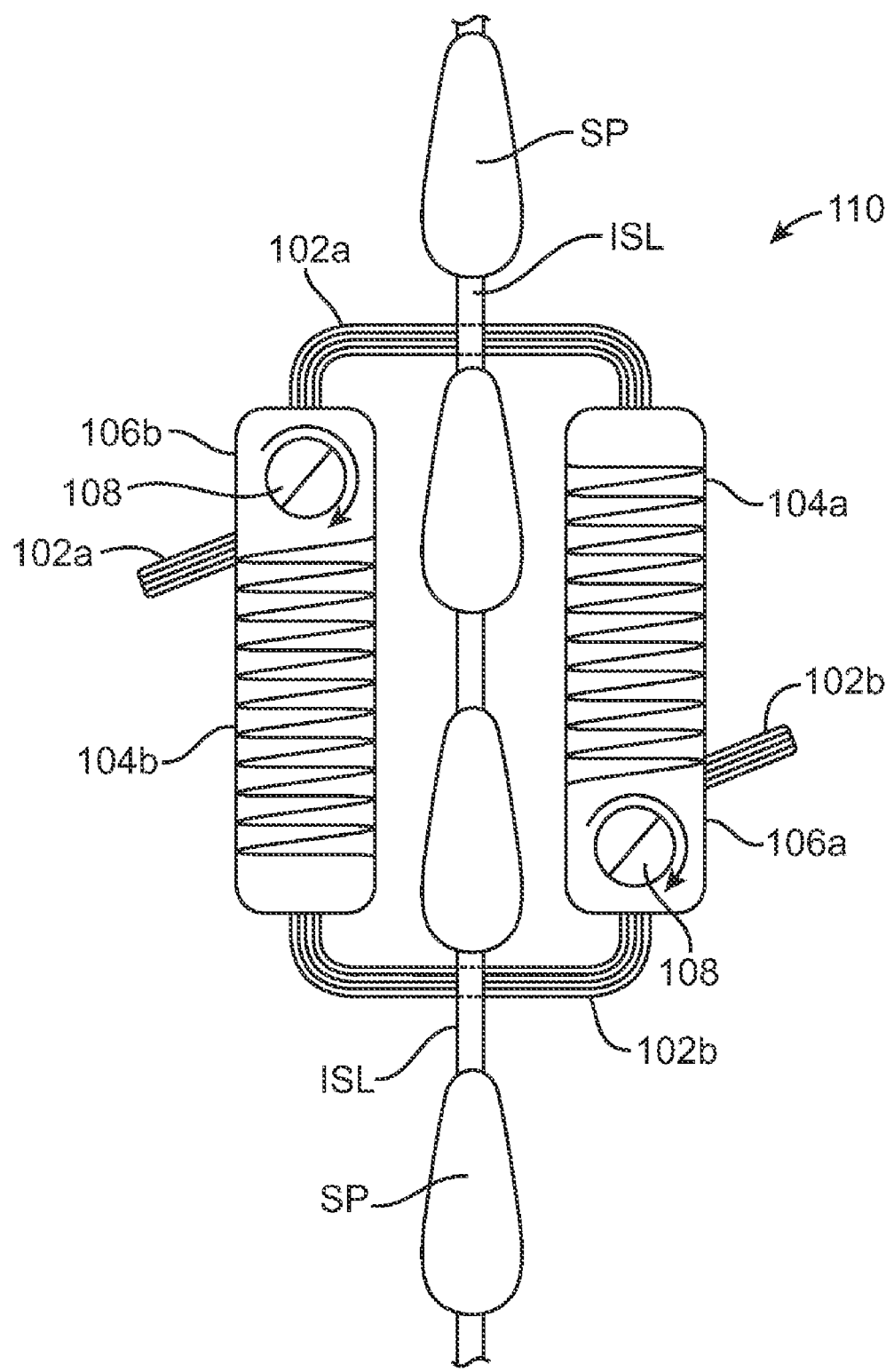

Fastening mechanism 106 may comprise a driver feature 108. As shown in FIG. 4L, the driver feature is adapted to receive a rotating driver tool RT. The driver feature may be a Phillips head, a slotted flat head, a Torx head, a hex head, or the like. Rotation of tool RT, which may be either clockwise or counter-clockwise, changes the configuration of fastening mechanism 106 so as to lock and secure tether 102 in place. This forms a continuous, multi-component tether structure or constraint 110 which couples two spinous processes SP together, as shown in FIG. 4M. Compliance elements 104a, 104b are used to control flexion between spinous processes SP while tethers 102a, 102b and respective fastening mechanisms 106a, 106b contribute to coupling the spinous processes SP together. Depending on the location of the perforations P1 and P2 and the lengths of the compliance elements 104a, 104b, constraint 110 may couple more than two spinous processes SP together. In general, compliance elements 104a, 104b comprise spring-like elements which will elastically elongate as tension is applied through tethers 102a, 102b in an axis generally parallel to the spine. As the spinous processes or spinous process and sacrum move apart during flexion of the constrained spinal segment, the superior tether 102a and inferior tether 102b will also move apart. Compliance elements 104a, 104b each include spring-like elements which will elastically resist the spreading with a force determined by the mechanical properties of the spring-like element. Thus, constraint 110 provides an elastic resistance to flexion of the spinal segment beyond the neutral position. Constraint 110 is often configured to provide a resistance in the range from 7.5 N/mm to 20 N/mm but the resistance may be below 3 N/mm or even below 0.5 N/mm. Constraint 110 may also be adjustable in certain dimensions to allow tightening over the spinous processes or spinous process and sacrum when the spinal segment is in a neutral position. Other, related tether embodiments and joining methods are disclosed in U.S. patent application Ser. No. 12/106,103, U.S. Patent Publication No. 2008/0009866, U.S. Patent Publication No. 2008/0108993U.S. patent application Ser. No. 12/106,049, and U.S. Provisional Patent Application No. 60/936,897, each of which, the entire contents are incorporated herein by reference.

Figure 5:
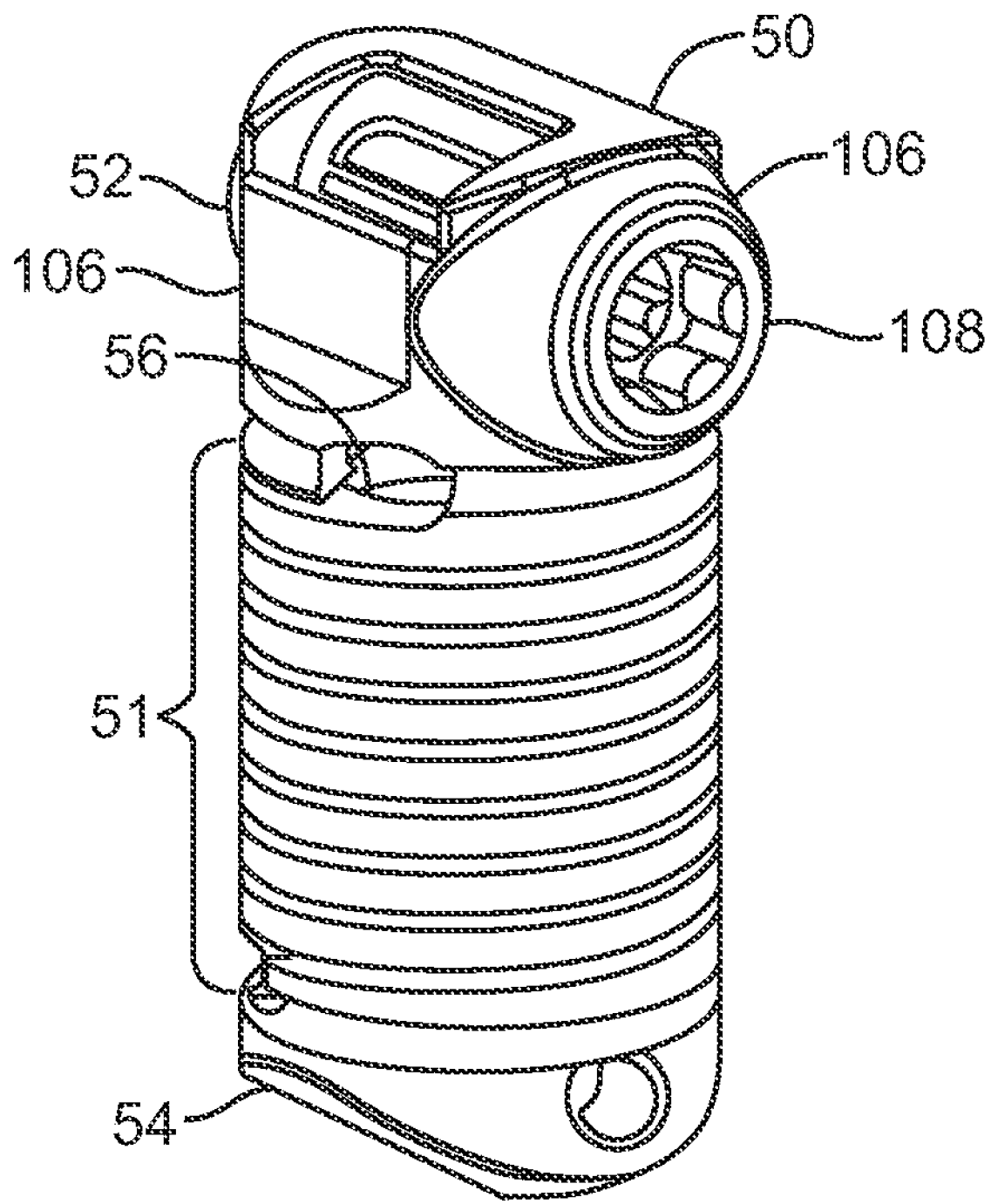
FIG. 5 illustrates an exemplary compliance element.

FIG. 5 illustrates an exemplary embodiment of a spring-like element 50 of compliance member 104a, 104b. Spring-like element 50 is generally similar to the spring-like elements disclosed in related, co-assigned U.S. patent application Ser. No. 12/106,103, the entire contents of which are incorporated herein by reference. Fastening mechanism 106 having a driver feature 108 is housed within spring-like element 50. Element 50 comprises a housing having a helical groove machined in the housing body to form the spring-like element. Element 50 includes an adjustable tether connector 52 and a fixed tether connector 54, both of which are preferably formed integrally or monolithically with the helical spring structure 51. Typically, the helical spring structure 51 and coupling portions of both tether connectors 52 and 54 will be formed from one piece of material, usually being a metal such as titanium, but optionally being a polymer, ceramic, reinforced glass or other composite, or other material having desired elastic and mechanical properties and capable of being formed into the desired geometry. In a preferred embodiment, spring-like element 50 is machined or laser cut from a titanium rod. Alternatively, a suitable polymeric material will be polyetherether ketone (PEEK). Other features may be built into the spring-like element 50, such as a stress relief hole 56. Components that compose the adjustable tether connector may potentially include a roller and a lock-nut; such components could be made from the same material as the element 50 and adjustable tether connector (e.g. titanium components if the spring-like element 50 is titanium), or they could be made from a different material (e.g. injection molded PEEK). The exterior of the spring-like element 50 may be covered with a protective cover, such as a sheath fabricated from an elastomer, polymer or other suitable material. The sheath may be placed over the body of the spring-like element 50 in order to prevent the intrusion of tissue and body fluids into the spaces between the turns of the coil and interior of the element.

Figure 6A:
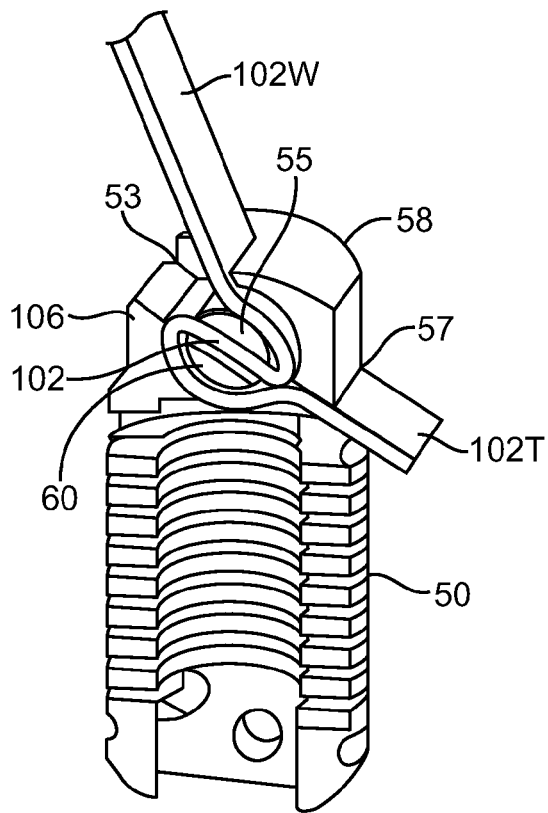
FIGS. 6A-6C illustrate the use of an exemplary fastening mechanism incorporated in the compliance element for removably locking a tether.

FIG. 6A shows a cross-section of spring-like element 50 having tether 102 locked therein. Tether 102 enters and exits the housing 58 of fastening mechanism 106 through entry aperture 53, then it passes through central channel 55, winds around roller 60 and the inside surface of housing 58, and finally exits through exit aperture 57. Roller 60 is housed within central channel 55 and is rotatable within tension element 50. Roller 60 is often substantially cylindrically shaped but may also have other shapes, for example, an eccentric shape. A round symmetrical roller will allow the tether 102 to spool evenly from both the working end and the tail end of the tether 102, while an eccentrically shaped roller will result in uneven spooling. The housing 58 of fastening mechanism 106 may be formed integrally with spring-like element 50 or may be separate.

Figure 6B:
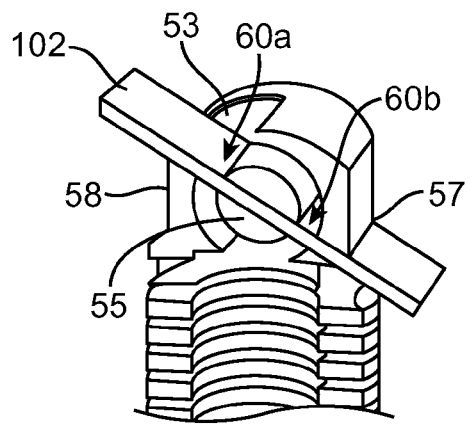
Figure 6C:
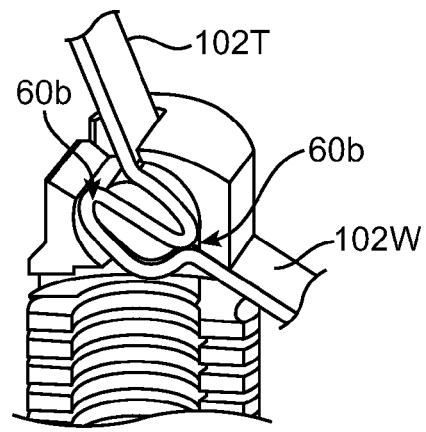

During a procedure similar to the one described with reference to FIGS. 4A-4M, tether 102 is advanced through top aperture 53, central channel 55 and roller 60, and out through bottom aperture 57. As shown in FIG. 6B, top aperture 53, central channel 55, and bottom aperture 57 are aligned so permit easy passage of tether 102 therethrough. Roller 60 includes two side apertures 60a, 60b. Prior to the locking of the tether, entry aperture 53, side apertures 60a and 60b and exit aperture 57 are all aligned along a common axis. To provide such alignment, roller 60 may include an alignment feature such as a pin or shoulder. Thus, the roller 60 may be rotated until stopped by the pin or shoulder, thereby ensuring alignment of all the apertures. Once tether 102 is advanced through, roller 60 is rotated, via driver feature 108, thus creating a friction-based interference fit between roller 60, the inside surface of the housing and the tether 102. As shown in FIG. 6C, the fastening mechanism is rotated approximately 180° to create this fit. The rotation of the roller creates a tortuous path for the tether as it passes between side apertures 60a, 60b. The rotation may retract the working end 102w and tail end 102t of tether 102, sometimes of different lengths, inward toward roller 60. Offsetting roller 60 from its axis of rotation by using an eccentrically shaped roller changes the amount of tether drawn from either side. The roller may also be rotated a selected amount in order to draw a desired amount of the tether into the roller. For example, the roller may be rotated from about ¼ turn to two or more complete revolutions. Thus, not only will the locking mechanism secure the tether in position, but it may also be used to help adjust length or tension of the tether.

A friction-based interference fit is advantageous because the range along the tether to which the mechanism can attach is continuous, rather than in discrete increments of non-friction mechanisms such as teeth, hooks, loops, and the like. Thus, forces between roller 60 and tether 102 are distributed along a longer portion of tether 102. Additionally, high clamping forces are not required. Thus, the risk that any specific point of contact will abrade, wear, or will otherwise be damaged is minimized. Furthermore, in contrast with other mechanisms that require high clamping forces, the discrete rotation of a tool is easier and more repeatable to perform during surgery.

After the tether is secured, roller 60 is then locked in place. Various means may be provided to lock roller 60 in place within housing 58. Roller 60 and/or the inner surface of housing 108 may include male or female threads which engage the two elements together. The threads may be partially deformed, thereby helping to secure the roller element with the housing. Alternatively, a pin 73 may be coupled to housing 58 and roller 60 may comprise a groove adapted to receive pin 73. Another possibility is that housing 58 may include a flange adapted to retain roller 60. A set screw as described below with reference to FIG. 7 may also be provided to lock roller 60 in place. Rotation of roller 60 in the opposite direction unwinds tether 102 from roller 60 and reduces the interference fit. Roller 60 and/or housing 58 may further include a position indicator, such as detents or calibration marks, to provide visual, tactile, or audible feedback to an operator on the relative position of the roller with respect to housing 58.

Figure 7:
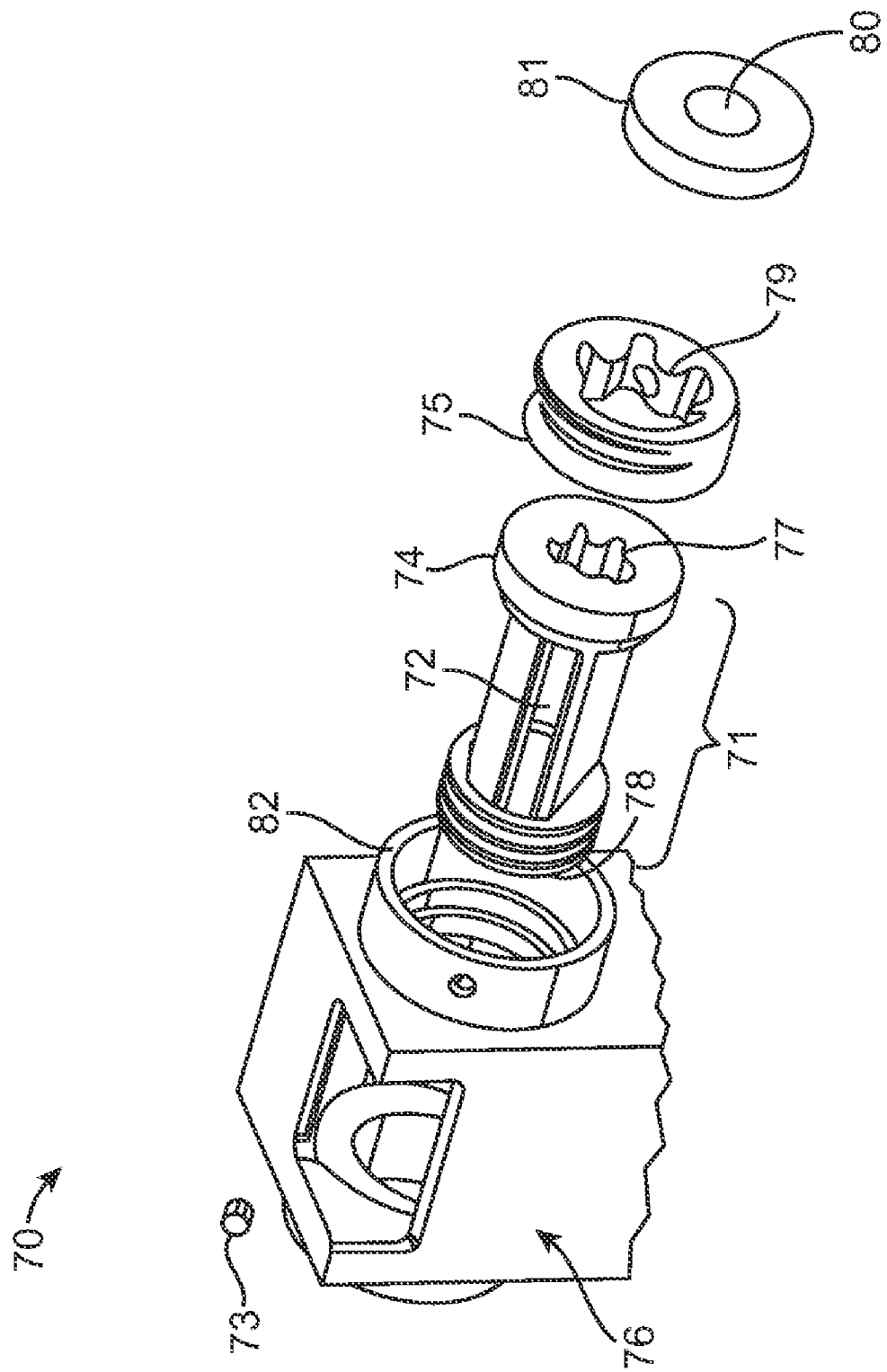
FIG. 7 is an exploded view of an exemplary fastening mechanism.

FIG. 7 shows an exploded view of an exemplary fastening mechanism 70 that uses a locking set screw 75 to lock roller 76 in place. Roller 71 is generally similar to roller 60. It is positioned within housing 76 and includes slots 72 for a tether to be advanced through. Roller 71 has threads 78 on one end that may be threadably engaged with the housing 76. Roller 71 also has a shoulder 74 and includes driver features 77. Shoulder 74 is adapted to be engageable with locking set screw 75 and housing 76. After roller 71 has been rotated to lock and secure a tether in place, set screw 75 is set in a position to engage roller 71 with housing 76 and hold it in position relative to housing 76. Shoulder 74, set screw 75, and/or housing 76 have threads to allow such engagement. The threads may be partially deformed, thereby further securing the locking member with the housing. The threads prevent the roller 71 from unrolling thereby allowing release of the tether. Set screw 75 may comprise driver features 79 to allow rotation of the set screw. Driver features 77 of roller 71 and driver features 79 of set screw 75 each are adapted to receive a tool so as to permit rotation thereof. The driver features 77, 79 may be a Phillips head, a slotted flat head, a Torx head, a hex head, or the like. Driver features 79 of set screw 75 may comprise an aperture large enough to permit access to roller 71 with a tool permit rotation of roller 71 with a tool while set screw 75 is engaged with housing 76. An optional end cap 81 having a central aperture 80 may be positioned adjacent the set screw 75 and welded, bonded or otherwise affixed to the outer rim 82 of the housing 76 so as to capture all the components forming an inseparable assembly. The aperture 80 is sized to allow access to rotation of the set screw. This is desirable since it prevents parts from falling out during use and also provides a device which is easier to use since assembly is not required. In preferred embodiments, the assembly may not be disassembled without breaking or otherwise damaging the device. In other embodiments, the assembly may be disassembled without damaging the device.

One advantage of the roller locking mechanisms disclosed herein is that the tether is not deformed in planes in which it lies. The tether may be folded or rolled in a plane transverse to the planes in which it lies. This is desirable since it minimizes the possibility of twisting or tangling of the tether and also reduces wear and tear.

Figure 8B:
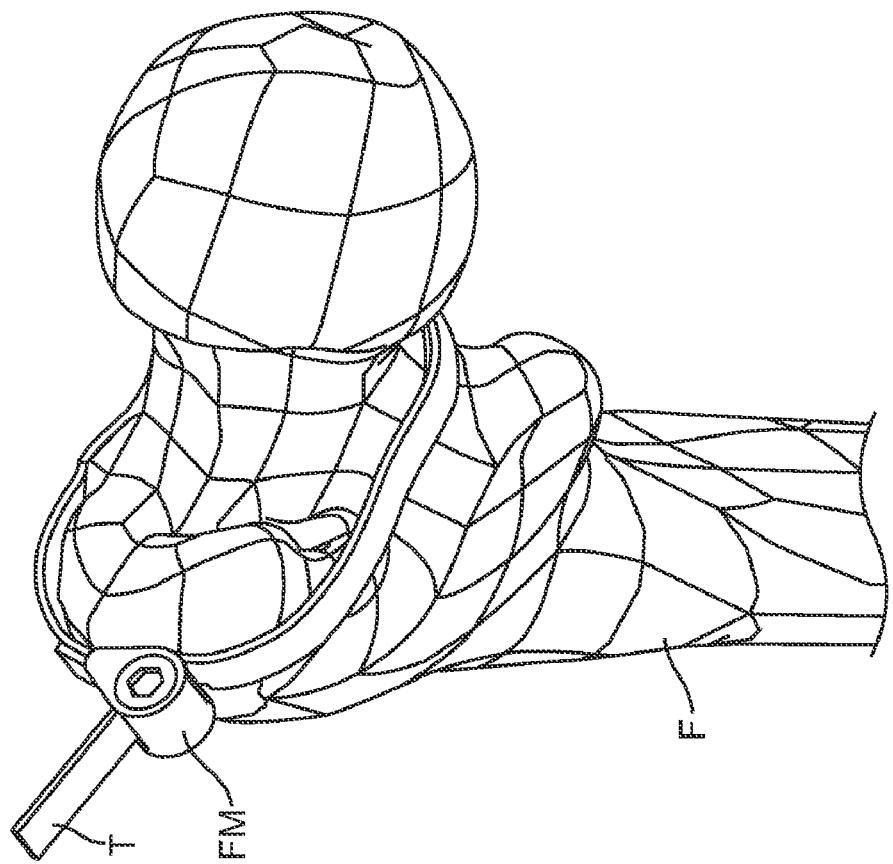
FIGS. 8A-8B illustrate the use of a tether and a fastening mechanism in trochanteric fracture fixation.
Figure 8A:
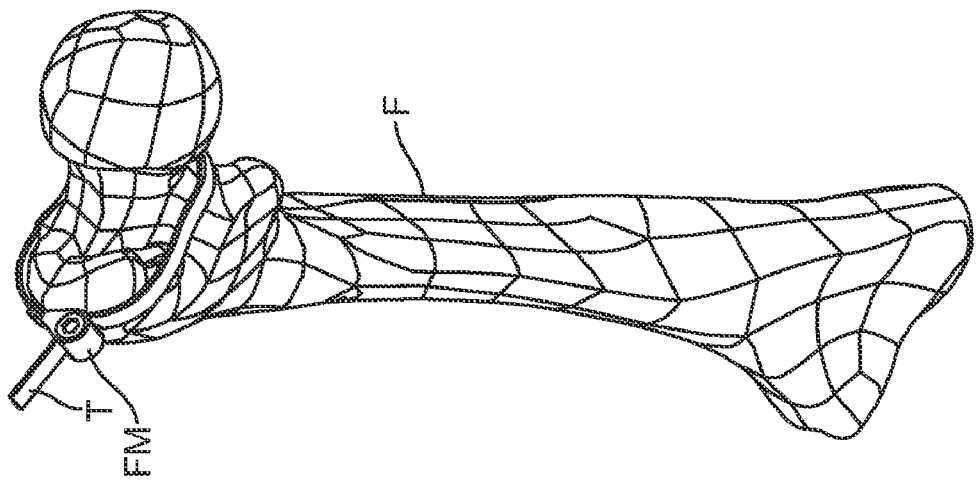

While the exemplary embodiments described above illustrate a fastening mechanism that is coupled with a spring-like compliance member, one will appreciate that the fastening mechanism may be used independently of a spring or other internal fixator. Other uses may include applications where a tether is secured with a knot, crimped or the like. These may include cerclage applications such as in trochanteric fixation in addition to application of a substantially rigid tether to multiple spinous processes or lamina. FIGS. 8A-8B illustrate the use of a tether and fastening mechanism for trochanteric fixation. FIG. 8A shows a tether T wrapped around the trochanter of a femur F. A fastening mechanism FM releasably locks one end of the tether T, thereby forming a closed loop around the trochanter. FIG. 8B highlights the tether wrapped around the trochanter.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A surgical fastening mechanism for releasably locking an implantable tether, said mechanism comprising:
a housing having a central channel therethrough, the housing also having a first side surface having an entry aperture, a second side surface having an exit aperture and a side channel extending therebetween;
a roller element having a first side with an entry aperture, a second side with an exit aperture and a roller channel therethrough, the roller element slidably disposed at least partially in the central channel such that the entry and exit apertures are at least partially aligned with the roller entry and exit apertures so as to permit free bidirectional passage of the tether therethrough, wherein rotation of the roller element in a first direction winds the tether about the roller element thereby creating a friction interface between the roller element, the housing and the tether as the tether passes through a tortuous path between the entry and exit apertures of the housing, the tortuous path comprising:
a first portion of the tether that enters the housing entry aperture and winds around an upper portion of the roller element, while maintaining contact with an inner surface of the housing;
a second portion of the tether that enters the roller pin entry aperture and passes through the roller channel towards the roller exit aperture;
a third portion of the tether that exits the roller exit aperture and winds around a lower portion of the roller element, while maintaining contact with the inner surface of the housing; and a fourth portion of the tether that exits the housing exit aperture; and
a locking mechanism operably connected with either the housing or the roller element, the locking mechanism adapted to prevent rotation of the roller in the central channel and adapted to prevent release of the tether from the roller; and
wherein the locking mechanism comprises a rotation limiting element coupled with the housing and wherein the housing comprises a receiver for receiving the rotation locking element, thereby limiting rotation of the roller relative to the housing.

2. The fastening mechanism of claim 1, wherein the roller element is threadably engaged with the housing.

3. The fastening mechanism of claim 2, wherein threads on either the roller element or the housing are partially deformed, thereby further securing the roller element with the housing.

4. The fastening mechanism of claim 1, wherein the roller locks the tether in position relative to the housing.

5. The fastening mechanism of claim 1, wherein the roller comprises a driver feature adapted to receive a tool to permit rotation of the roller element.

6. The fastening mechanism of claim 1, wherein the housing comprises a flange adapted to retain the roller element.

7. The fastening mechanism of claim 1, wherein the roller element comprises an alignment feature adapted to align the roller aperture with the first and second side apertures in the housing.

8. The fastening mechanism of claim 7, wherein the roller element is threadably engaged with the housing and the alignment feature constrains longitudinal movement of the roller element in the central channel, thereby also limiting rotation of the roller element.

9. The fastening mechanism of claim 1, wherein the roller element comprises an alignment feature adapted to limit rotation of the roller element relative to the housing.

10. The fastening mechanism of claim 1, wherein the roller element is rotationally disposed in the central channel.

11. The fastening mechanism of claim 1, wherein the locking mechanism comprises a friction fit between the roller element and the housing.

12. The fastening mechanism of claim 1, wherein the locking mechanism comprises a set screw threadably engaged with the housing.

13. The fastening mechanism of claim 1, wherein the housing, the roller element and the locking mechanism are held together and are inseparable from one another while the fastening mechanism is undamaged.

14. The fastening mechanism of claim 1, wherein threads on either the locking mechanism or the housing are partially deformed, thereby further securing the locking member with the housing.

15. The fastening mechanism of claim 1, wherein the set screw is engaged against the roller element.

16. The fastening mechanism of claim 1, wherein the set screw comprises a driver feature adapted to receive a tool to permit rotation of the set screw.

17. The fastening mechanism of claim 16, wherein the driver feature on the set screw comprises an aperture large enough to permit access to the roller element with a tool for rotation thereof while the set screw is threadably engaged with the housing.

18. The fastening mechanism of claim 1 wherein the locking mechanism is frictionally engaged with the roller and the housing.

19. The fastening mechanism of claim 1, wherein the roller is frictionally engaged with the housing.

20. The fastening mechanism of claim 1, wherein the housing comprises a flange adapted to retain the locking mechanism.

21. The fastening mechanism of claim 1, wherein the housing comprises an elastic element.

22. The fastening mechanism of claim 1, wherein the entry and exit apertures are shaped like rectangular slots.

23. The fastening mechanism of claim 1, wherein the housing comprises an alignment feature adapted to align the roller aperture with the first and second side apertures in the housing.

24. The fastening mechanism of claim 23, wherein the alignment feature comprises a pin or a shoulder coupled with either the housing or the roller element.

25. The fastening mechanism of claim 1, wherein the housing comprises third and fourth outer surfaces and the central channel extends from the third outer surface to the fourth outer surface.

26. The fastening mechanism of claim 1, wherein the roller element is rotated approximately 180 degrees in order to create the friction fit.

27. The fastening mechanism of claim 1, wherein the roller element is adapted to be rotated a selected amount so as to retract a desired length of the tether into the housing.

28. The fastening mechanism of claim 1, wherein rotation of the roller locks the tether so as to fix the tether's position relative to the housing.

29. The fastening mechanism of claim 1, wherein rotation of the roller element in a second direction opposite of the first direction unwinds the tether therefrom thereby reducing the interference fit between the roller element and the housing.

30. The fastening mechanism of claim 1, further comprising a position indicator adapted to provide visual, tactile or audible feedback to an operator on the relative position of the roller with respect to the housing.

31. The fastening mechanism of claim 1, wherein the tether remains undeformed along planes in which the tether lies, and wherein the tether is only deformed along a plane transverse to planes in which the tether lies.

32. The fastening mechanism of claim 1, wherein the implantable tether comprises a spinous process constraint device adapted to limit flexion between adjacent spinous processes or between a spinous process and a sacrum.

33. The fastening mechanism of claim 1, wherein the implantable tether comprises a tether adapted to hold two or more anatomic structures together.

34. A surgical fastening mechanism for releasably locking an implantable tether, said mechanism comprising:
a housing having a central channel therethrough, the housing also having a first side surface having an entry aperture, a second side surface having an exit aperture and a side channel extending therebetween;
a roller element having a first side with an entry aperture, a second side with an exit aperture and a roller channel therethrough, the roller element slidably disposed at least partially in the central channel such that the entry and exit apertures are at least partially aligned with the roller entry and exit apertures so as to permit free bidirectional passage of the tether therethrough, wherein rotation of the roller element in a first direction winds the tether about the roller element thereby creating a friction interface between the roller element, the housing and the tether as the tether passes through a tortuous path between the entry and exit apertures of the housing, the tortuous path comprising:
a first portion of the tether that enters the housing entry aperture and winds around an upper portion of the roller element, while maintaining contact with an inner surface of the housing;
a second portion of the tether that enters the roller pin entry aperture and passes through the roller channel towards the roller exit aperture;
a third portion of the tether that exits the roller exit aperture and winds around a lower portion of the roller element, while maintaining contact with the inner surface of the housing; and a fourth portion of the tether that exits the housing exit aperture; and
a locking mechanism operably connected with either the housing or the roller element, the locking mechanism adapted to prevent rotation of the roller in the central channel and adapted to prevent release of the tether from the roller; and
wherein the roller element is frictionally engaged with the housing.

35. The fastening mechanism of claim 34, wherein the roller element is threadably engaged with the housing.

36. The fastening mechanism of claim 35, wherein threads on either the roller element or the housing are partially deformed, thereby further securing the roller element with the housing.

37. The fastening mechanism of claim 34, wherein the roller locks the tether in position relative to the housing.

38. The fastening mechanism of claim 34, wherein the roller comprises a driver feature adapted to receive a tool to permit rotation of the roller element.

39. The fastening mechanism of claim 34, wherein the housing comprises a flange adapted to retain the roller element.

40. The fastening mechanism of claim 34, wherein the roller element comprises an alignment feature adapted to align the roller aperture with the first and second side apertures in the housing.

41. The fastening mechanism of claim 40, wherein the alignment feature comprises a pin or a shoulder.

42. The fastening mechanism of claim 40, wherein the roller element is threadably engaged with the housing and the alignment feature constrains longitudinal movement of the roller element in the central channel, thereby also limiting rotation of the roller element.

43. The fastening mechanism of claim 34, wherein the roller element comprises an alignment feature adapted to limit rotation of the roller element relative to the housing.

44. The fastening mechanism of claim 34, wherein the roller element is rotationally disposed in the central channel.

45. The fastening mechanism of claim 34, wherein the locking mechanism comprises a friction fit between the roller element and the housing.

46. The fastening mechanism of claim 34, wherein the locking mechanism comprises a set screw threadably engaged with the housing.

47. The fastening mechanism of claim 46, wherein threads on either the locking mechanism or the housing are partially deformed, thereby further securing the locking member with the housing.

48. The fastening mechanism of claim 46, wherein the set screw is engaged against the roller element.

49. The fastening mechanism of claim 46, wherein the set screw comprises a driver feature adapted to receive a tool to permit rotation of the set screw.

50. The fastening mechanism of claim 49, wherein the driver feature on the set screw comprises an aperture large enough to permit access to the roller element with a tool for rotation thereof while the set screw is threadably engaged with the housing.

51. The fastening mechanism of claim 34, wherein the housing, the roller element and the locking mechanism are held together and are inseparable from one another while the fastening mechanism is undamaged.

52. The fastening mechanism of claim 34, further comprising a pin coupled with the housing and wherein the locking mechanism comprises a groove adapted to receive the pin, thereby locking the locking member with the housing.

53. The fastening mechanism of claim 34, wherein the locking mechanism is frictionally engaged with the roller and the housing.

54. The fastening mechanism of claim 34, wherein the locking mechanism comprises a rotation limiting element coupled with the housing and wherein the housing comprises a receiver for receiving the rotation locking element, thereby limiting rotation of the roller relative to the housing.

55. The fastening mechanism of claim 34, wherein the housing comprises a flange adapted to retain the locking mechanism.

56. The fastening mechanism of claim 34, wherein the housing comprises an elastic element.

57. The fastening mechanism of claim 34, wherein the entry and exit apertures are shaped like rectangular slots.

58. The fastening mechanism of claim 34, wherein the housing comprises an alignment feature adapted to align the roller aperture with the first and second side apertures in the housing.

59. The fastening mechanism of claim 58, wherein the alignment feature comprises a pin or a shoulder coupled with either the housing or the roller element.

60. The fastening mechanism of claim 34, wherein the housing comprises third and fourth outer surfaces and the central channel extends from the third outer surface to the fourth outer surface.

61. The fastening mechanism of claim 34, wherein the roller element is rotated approximately 180 degrees in order to create the friction fit.

62. The fastening mechanism of claim 34, wherein the roller element is adapted to be rotated a selected amount so as to retract a desired length of the tether into the housing.

63. The fastening mechanism of claim 34, wherein rotation of the roller locks the tether so as to fix the tether's position relative to the housing.

64. The fastening mechanism of claim 34, wherein rotation of the roller element in a second direction opposite of the first direction unwinds unwinds the tether therefrom thereby reducing the interference fit between the roller element and the housing.

65. The fastening mechanism of claim 34, further comprising a position indicator adapted to provide visual, tactile or audible feedback to an operator on the relative position of the roller with respect to the housing.

66. The fastening mechanism of claim 34, wherein the tether remains undeformed along planes in which the tether lies, and wherein the tether is only deformed along a plane transverse to planes in which the tether lies.

67. The fastening mechanism of claim 34, wherein the implantable tether comprises a spinous process constraint device adapted to limit flexion between adjacent spinous processes or between a spinous process and a sacrum.

68. The fastening mechanism of claim 34, wherein the implantable tether comprises a tether adapted to hold two or more anatomic structures together.

69. A surgical fastening mechanism for releasably locking an implantable tether, said mechanism comprising:
  a housing having a central channel therethrough, the housing also having a first side surface having an entry aperture, a second side surface having an exit aperture and a side channel extending there between;
  a roller element having a first side with an entry aperture, a second side with an exit aperture and a roller channel therethrough, the roller element slidably disposed at least partially in the central channel such that the entry and exit apertures are at least partially aligned with the roller entry and exit apertures so as to permit free bidirectional passage of the tether therethrough, wherein rotation of the roller element in a first direction winds the tether about the roller element thereby creating a friction interface between the roller element, the housing and the tether as the tether passes through a tortuous path between the entry and exit apertures of the housing, the tortuous path comprising:
  a first portion of the tether that enters the housing entry aperture and winds around an upper portion of the roller element, while maintaining contact with an inner surface of the housing;
  a second portion of the tether that enters the roller pin entry aperture and passes through the roller channel towards the roller exit aperture;

a third portion of the tether that exits the roller exit aperture and winds around a lower portion of the roller element, while maintaining contact with the inner surface of the housing; and a fourth portion of the tether that exits the housing exit aperture; and a locking mechanism operably connected with either the housing or the roller element, the locking mechanism adapted to prevent rotation of the roller in the central channel and adapted to prevent release of the tether from the roller; and wherein rotation of the roller element in a second direction opposite of the first direction unwinds the tether therefrom thereby reducing the interference fit between the roller element and the housing.

70. The fastening mechanism of claim 69, wherein the roller element is threadably engaged with the housing.

71. The fastening mechanism of claim 70, wherein threads on either the roller element or the housing are partially deformed, thereby further securing the roller element with the housing.

72. The fastening mechanism of claim 69, wherein the roller locks the tether in position relative to the housing.

73. The fastening mechanism of claim 69, wherein the roller comprises a driver feature adapted to receive a tool to permit rotation of the roller element.

74. The fastening mechanism of claim 69, wherein the housing comprises a flange adapted to retain the roller element.

75. The fastening mechanism of claim 69, wherein the roller element comprises an alignment feature adapted to align the roller aperture with the first and second side apertures in the housing.

76. The fastening mechanism of claim 75, wherein the roller element is threadably engaged with the housing and the alignment feature constrains longitudinal movement of the roller element in the central channel, thereby also limiting rotation of the roller element.

77. The fastening mechanism of claim 69, wherein the roller element comprises an alignment feature adapted to limit rotation of the roller element relative to the housing.

78. The fastening mechanism of claim 69, wherein the roller element is rotationally disposed in the central channel.

79. The fastening mechanism of claim 69, wherein the locking mechanism comprises a friction fit between the roller element and the housing.

80. The fastening mechanism of claim 69, wherein the locking mechanism comprises a set screw threadably engaged with the housing.

81. The fastening mechanism of claim 80, wherein threads on either the locking mechanism or the housing are partially deformed, thereby further securing the locking member with the housing.

82. The fastening mechanism of claim 80, wherein the set screw is engaged against the roller element.

83. The fastening mechanism of claim 80, wherein the set screw comprises a driver feature adapted to receive a tool to permit rotation of the set screw.

84. The fastening mechanism of claim 83, wherein the driver feature on the set screw comprises an aperture large enough to permit access to the roller element with a tool for rotation thereof while the set screw is threadably engaged with the housing.

85. The fastening mechanism of claim 69, wherein the housing, the roller element and the locking mechanism are held together and are inseparable from one another while the fastening mechanism is undamaged.

86. The fastening mechanism of claim 69, wherein the locking mechanism is frictionally engaged with the roller and the housing.

87. The fastening mechanism of claim 69, wherein the roller is frictionally engaged with the housing.

88. The fastening mechanism of claim 69, wherein the locking mechanism comprises a rotation limiting element coupled with the housing and wherein the housing comprises a receiver for receiving the rotation locking element, thereby limiting rotation of the roller relative to the housing.

89. The fastening mechanism of claim 69, wherein the housing comprises a flange adapted to retain the locking mechanism.

90. The fastening mechanism of claim 69, wherein the housing comprises an elastic element.

91. The fastening mechanism of claim 69, wherein the entry and exit apertures are shaped like rectangular slots.

92. The fastening mechanism of claim 69, wherein the housing comprises an alignment feature adapted to align the roller aperture with the first and second side apertures in the housing.

93. The fastening mechanism of claim 92, wherein the alignment feature comprises a pin or a shoulder coupled with either the housing or the roller element.

94. The fastening mechanism of claim 69, wherein the housing comprises third and fourth outer surfaces and the central channel extends from the third outer surface to the fourth outer surface.

95. The fastening mechanism of claim 69, wherein the roller element is rotated approximately 180 degrees in order to create the friction fit.

96. The fastening mechanism of claim 69, wherein the roller element is adapted to be rotated a selected amount so as to retract a desired length of the tether into the housing.

97. The fastening mechanism of claim 69, wherein rotation of the roller locks the tether so as to fix the tether's position relative to the housing.

98. The fastening mechanism of claim 69, further comprising a position indicator adapted to provide visual, tactile or audible feedback to an operator on the relative position of the roller with respect to the housing.

99. The fastening mechanism of claim 69, wherein the tether remains undeformed along planes in which the tether lies, and wherein the tether is only deformed along a plane transverse to planes in which the tether lies.

100. The fastening mechanism of claim 69, wherein the implantable tether comprises a spinous process constraint device adapted to limit flexion between adjacent spinous processes or between a spinous process and a sacrum.

101. The fastening mechanism of claim 69, wherein the implantable tether comprises a tether adapted to hold two or more anatomic structures together.

* * * * *